United States Patent
Mitrani

(10) Patent No.: US 12,377,121 B2
(45) Date of Patent: *Aug. 5, 2025

(54) COMPOSITIONS COMPRISING NANOPARTICLES, METHOD OF MAKING AND USES THEREOF

(71) Applicant: Organicell Regenerative Medicine, Inc., Miami, FL (US)

(72) Inventor: Maria Ines Mitrani, Miami Beach, FL (US)

(73) Assignee: Zeo ScientifiX, Inc., Fort Lauderdale, FL (US)

( * ) Notice: Subject to any disclaimer, the term of this patent is extended or adjusted under 35 U.S.C. 154(b) by 582 days.

This patent is subject to a terminal disclaimer.

(21) Appl. No.: 17/226,587

(22) Filed: Apr. 9, 2021

(65) Prior Publication Data

US 2021/0315939 A1 Oct. 14, 2021

Related U.S. Application Data

(60) Provisional application No. 63/008,355, filed on Apr. 10, 2020.

(51) Int. Cl.
| | |
|---|---|
| *A61K 35/50* | (2015.01) |
| *A61K 9/51* | (2006.01) |
| *A61K 31/7105* | (2006.01) |
| *A61K 45/06* | (2006.01) |
| *A61P 11/00* | (2006.01) |
| *A61P 19/02* | (2006.01) |
| *B82Y 5/00* | (2011.01) |

(52) U.S. Cl.
CPC ............... *A61K 35/50* (2013.01); *A61K 9/51* (2013.01); *A61K 31/7105* (2013.01); *A61K 45/06* (2013.01); *A61P 11/00* (2018.01); *A61P 19/02* (2018.01); *B82Y 5/00* (2013.01)

(58) Field of Classification Search
None
See application file for complete search history.

(56) References Cited

U.S. PATENT DOCUMENTS

| | | |
|---|---|---|
| 2017/0100439 A1 | 4/2017 | Harrell |
| 2018/0250343 A1 | 9/2018 | Reems et al. |
| 2019/0290696 A1 | 9/2019 | De Miroschedji et al. |
| 2020/0179827 A1 | 6/2020 | Deregibus et al. |
| 2020/0264185 A1 | 8/2020 | Xu et al. |
| 2020/0289583 A1 | 9/2020 | Ferreira et al. |

FOREIGN PATENT DOCUMENTS

| | | |
|---|---|---|
| JP | 2019517597 | 6/2019 |
| WO | WO2013082487 | 6/2013 |
| WO | 2017/003954 A1 | 1/2017 |
| WO | 2017/165698 A1 | 9/2017 |
| WO | WO2017218535 | 12/2017 |

OTHER PUBLICATIONS

Bazrafshan et al. (2014) J. Surg. Res. 188: 545-552. (Year: 214).*
Antounians et al. (2019) Scientific Reports 9: 1837 (11 pages) (Year: 2019).*
Balbi et al. (2017) Stem Cells Translational Medicine 6: 1340-1355. (Year: 2017).*
Herretes et al. (2006) American J. Ophthamology Aug. 2006: 271-278. (Year: 2006).*
Sheller-Miller et al. (2020) Methods in Enzymology, vol. 645: 181-194. (Year: 2020).*
U.S. Appl. No. 17/990,522, filed Nov. 18, 2022, Mitrani et al.
U.S. Appl. No. 18/063,227, filed Nov. 8, 2022, Mitrani et al.
Hovius et al., "The urokinase receptor (uPAR) facilitates clearance of Borrelia burgdorferi", PLoS Pathogens, May 2009, pp. 1-14, vol. 5(5).
Arend, William P., "The balance between IL-1 and IL-1Ra in disease", Cytokine Growth Factor Reviews, 2002; pp. 323-340, vol. 13.
Achari et al., "Adiponectin, a Therapeutic Target for Obesity, Diabetes, and Endothelial Dysfunction", International Journal of Molecular Sciences, Jun. 21, 2017, pp. 1-17, vol. 18(1321).
Johns et al., Growth factor effects on costal chondrocytes for tissue engineering fibrocartilage, Cell Tissue Res., Sep. 2008, pp. 439-447, vol. 333(3).
Koike et al., "Characterization of amniotic stem cells", Cellular Reprograming, 2014, pp. 16:298-305, vol.(4).
Murphy et al., "Isolation, Cryopreservation and Culture of Human Amnion Epithelial Cells for Clinical Applications", Journal of Visualized Experiments, Dec. 2014, pp. 1-8, e52085, vol. 94.
Reiter et al., "Stromal derived factor-1 mediates the lung regenerative effects of mesenchymal stem cells in a rodent model of bronchopulmonary dysplasia", Respiratory Researh, 2017, pp. 1-11 vol. 18(137).
Liu et al., "The cytokine storm of severe influenza and development of immunomodulatory therapy", Cellular & Molecular Immunology, 2016; pp. 3-10, vol. 13.
Wu et al., "Risk Factors Associated With Acute Respiratory Distress Syndrome and Death in Patients With Coronavirus Disease 2019 Pneumonia in Wuhan, China", JAMA Internal Medicine, Mar. 13, 2020, pp. 934-943, vol. 180(7).
Malda, Jos, et al, Nat Rev Rheumatol—Extracellular Vesicles—New Tool for Joint Repair and Regeneration (2016, 12(4), 243-9 (Year 2016).
Usman, Waqas Muhammad, et al, Nature Communications—Efficient RNA Drug Delivery Using Red Blood Cell Extracellular Vesicles (2018, 9:2359, 1-15) (Year: 2018).

(Continued)

*Primary Examiner* — Russell G Fiebig
(74) *Attorney, Agent, or Firm* — Malloy & Malloy, P.L.; W. John Eagan

(57) ABSTRACT

Presented herein, in certain aspects, are cell-free therapeutic composition derived from human amniotic fluid (HAF) and uses thereof for the prevention and treatment of selected diseases and disorders.

43 Claims, 22 Drawing Sheets

(20 of 22 Drawing Sheet(s) Filed in Color)

(56) References Cited

OTHER PUBLICATIONS

C. Luke Dixon et al., Amniotic fluid exosome proteomic profile exhibits unique pathways of term and preterm labor; Endocrinology, vol. 159, No. 5, pp. 2229-2240, Apr. 4, 2018.
Manuela Zavatti et al., Comparison of the therapeutic effect of amniotic fluid stem cells and their exosomes on monoiodoacetate-induced animal model of osteoarthritis; BioFactors, vol. 46, No. 1, pp. 106-117, Oct. 18, 2019.
Juntao Xie et al., The relationship between amniotic fluid miRNAs and congenital obstructive nephropathy; Am J Transl Res, vol. 9, No. 7, pp. 1754-1763, Apr. 30, 2017.
Patent Cooperation Treaty, International Search Report issued in PCT/IB2021/052982, Jul. 15, 2021, pp. 1-2.
Dixon et al., "Amniotic fluid exosome proteomic profile exhibits unique pathways of term and preterm labor", Endocrinology, 2018, pp. 2229-2240, vol. 159(5).
Xie et al., "The relationship between amniotic fluid miRNAs and congenital obstructive nephropathy, American journal of translational research", 2017, pp. 1754-1763, vol. 9(4).

\* cited by examiner

Exosomal Marker CD63 Concentration in Flow-XL vs Flow Control

Protein Concentration

Fig. 9    Exosome surface marker detection
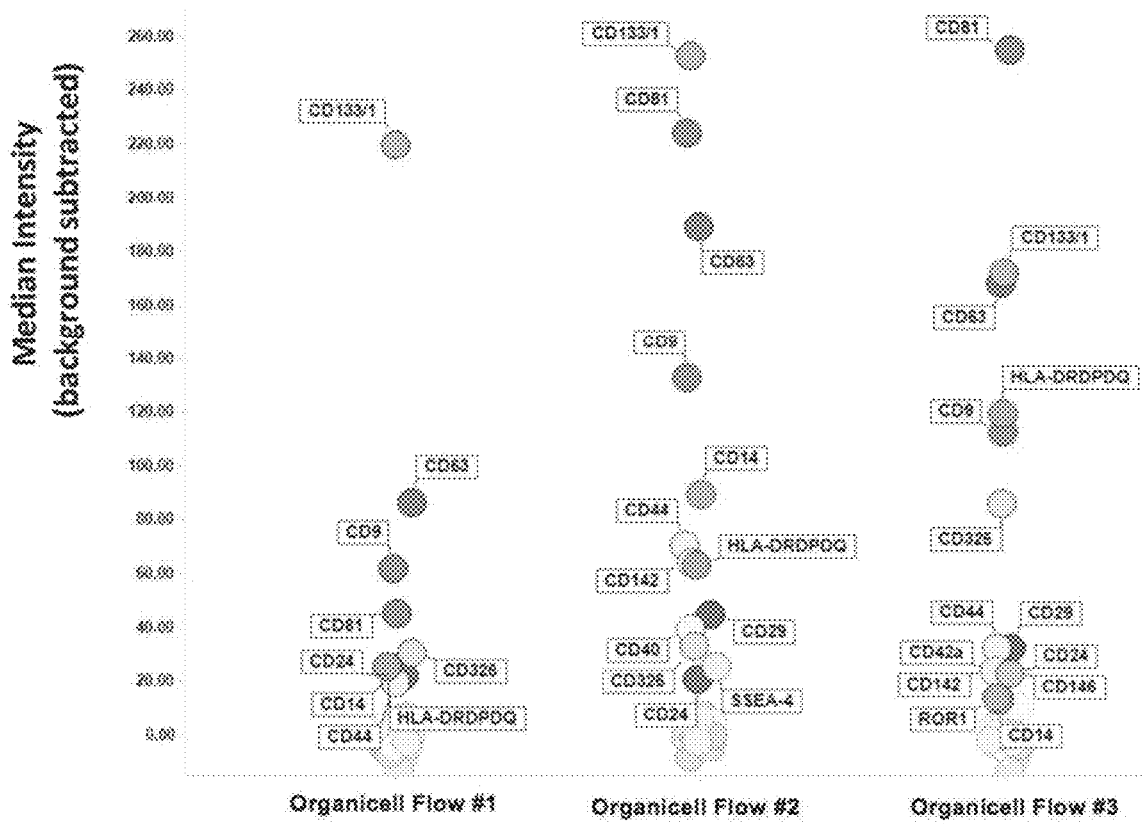
Fig. 10    Organicell Flow Exosome Surface Marker Profile
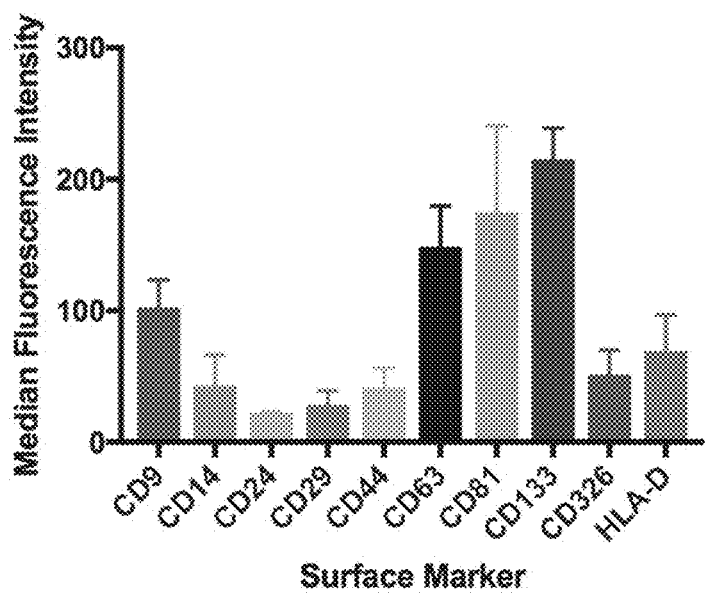

Protien Types Identified in Organicell Flow Exosomes

COMPOSITIONS COMPRISING NANOPARTICLES, METHOD OF MAKING AND USES THEREOF

RELATED APPLICATIONS

This application claims priority to U.S. Provisional Patent Application No. 63/008,355, filed Apr. 10, 2020, the contents of which are incorporated herein by reference in its entirety,

SUMMARY

In certain aspects, provided herein is a cell-free therapeutic composition comprising a modified human amniotic fluid (HAF). In certain aspects, provided herein is a cell-free therapeutic composition comprising (a) a modified human amniotic fluid (HAF); and (b) HAF-derived nanoparticles; where the nanoparticles have a diameter of greater than 50 nm, and the concentration of the particles in the composition is at least $1 \times 10^8$ particles/ml.

Also, presented herein in certain aspects is a method of treating a lung disease or lung disorder in a subject in need thereof, comprising administering to the subject a therapeutically effective amount of a therapeutic composition disclosed herein, wherein the lung disease or disorder is selected from acute respiratory syndrome, chronic obstructive pulmonary disease (COPD), and bronchopulmonary dysplasia.

Also, presented herein, in certain aspects, is a method of preventing or treating arthritis in a subject in need thereof, comprising administering to the subject a therapeutically effective amount of a therapeutic composition disclosed herein. In certain embodiments, the arthritis is osteoarthritis or rheumatoid arthritis.

Also, presented herein, in certain aspects, is a method of preventing or treating acute brain injury in a subject in need thereof, comprising administering to the subject a therapeutically effective amount of a therapeutic composition disclosed herein. In certain embodiments, the acute brain injury may be caused by acute respiratory syndrome coronavirus, such as COVID-19.

Also, presented herein, in certain aspects, is a method of preventing or treating acute organ failure in a subject in need thereof, comprising administering to the subject a therapeutically effective amount of a therapeutic composition disclosed herein. In certain embodiments, the acute organ failure or acute sequential organ failure may be caused by acute respiratory syndrome coronavirus, such as COVID-19.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments. The patent or application file contains at least one drawing executed in color. Copies of this patent or patent application publication with color drawing(s) will be provided by the Office upon request and payment of the necessary fee.

FIG. 1A shows a nanoparticle distribution of an embodiment of Organicell Flow. FIG. 1B shows a nanoparticle distribution of an embodiments of Organicell Flow-XL. FIG. 1C shows a nanoparticle concentration comparison between Organicell Flow and Organicell Flow-XL. Connection lines with a positive slope are representative of increased nanoparticle concentration between Flow-XL and Flow (N=4, p-value<0.005, t-test).

FIG. 9 shows a representative analysis of exosome (nanoparticle) surface markers showing their relative amount on isolated exosomes.

FIG. 10 shows the average median fluorescence intensity (Y-axis) of positively expressed surface markers on isolated exosomes (number of products analyzed=3).

FIG. 16A shows the effect of Organicell Flow-XL (amniotic exosome) compared to saline control (PBS) in Normoxia (open bars) and Hyperoxia conditions (black bars) on right ventricular systolic pressure (RVSP). FIG. 16B shows the effect of Organicell Flow-XL (amniotic exosome) compared to saline control (PBS) in normoxia (open bars) and hyperoxia conditions (black bars) on right ventricular hypertrophy (n=4 for saline, n=11 for flow-XL, **p-value<0.005).

DETAILED DESCRIPTION OF THE INVENTION

Figure 1A:
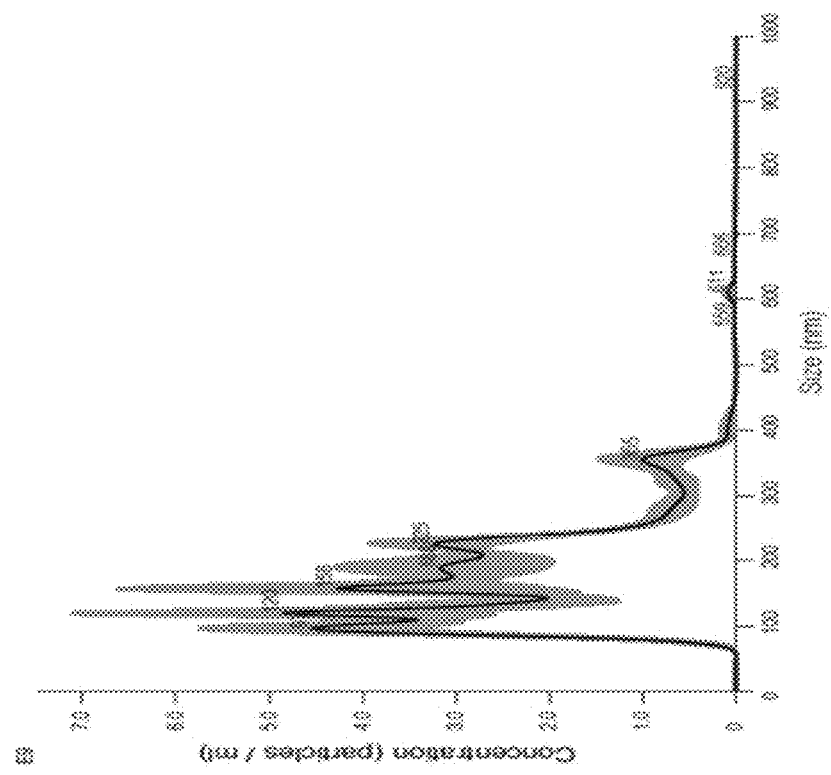
FIGS. 1A-1C show a nanoparticle analysis of Organicell Flow and Organicell Flow-XL.

Presented herein, in part, are novel cell-free therapeutic compositions derived from human amniotic fluid (HAF). HAF is a partially characterized protective fluid contained within the amniotic sac that surrounds a fetus during pregnancy. HAF contains a complex mixture of water, salts, proteins, carbohydrates, lipids, phospholipids, urea, cytokines, growth factors, lactate, pyruvate, enzymes, hormones, taurine, amino acids, lactoferrin debris and cells. HAF also contains fine hair derived from the fetus known as lanugo, and *vernix*, a waxy or cheese-like white substance found coating the skin of a fetus. *Vernix* is produced by dedicated fetal cells and confers a protective role during fetal development and for a few hours after birth. As used herein, the term "substantially" is intended to have the meaning commonly understood by those of skill in the art to which this invention pertains.

HAF also includes cells. The variety of cells found in HAF include cells from fetal skin, respiratory, digestive, and urinary tracts, and cells derived from the amniotic membrane, as well as macrophages, hematopoietic progenitor and stem cells. The hematopoietic progenitor and stem cells are thought to confer healing, regenerative, and developmental properties to HAF while macrophages are thought to provide some level of immune defense. Some cells isolated from HAF express neural markers, such as Nestin, β3-tubulin, GFAP, NEFH, as well as several markers of embryonic stem cells (ESCs), such as SSEA-4, Oct4, and Nanog. These cells exhibit osteogenic, adipogenic, myogenic and neural differentiation. They can also differentiate into hepatocytes and endothelial cells.

Compositions

Presented herein are HAF-derived compositions, referred to herein as therapeutic compositions. However, the therapeutic compositions provided herein are distinctly different than naturally occurring HAF in both content and function. In some embodiments a therapeutic composition is cell-free or is substantially free of cells. Accordingly, in certain embodiments, a therapeutic composition does not contain a eukaryotic cell or a prokaryotic cell. In certain embodiments, a therapeutic composition does not contain a eukaryotic cell, non-limiting examples of which include maternal-derived cells, fetal-derived cells, placenta-derived cells, red blood cells, nucleated cells, white blood cells or leukocytes, macrophages, hematopoietic progenitor cells, stem cells, epithelial cells, the like and combinations thereof. In certain embodiments, a therapeutic composition does not contain a prokaryotic cell, non-limiting examples of which include bacterial cells, non-limiting examples of which include *Propionibacterium* spp. (e.g., *P. acnes*), *Corynebacterium* spp., *Brevibacterium* spp., and *Staphylococcus* spp. (e.g., *S. epidermidis*).

In certain embodiments, a therapeutic composition does not contain a pathogen, non-limiting examples of which include a virus, a bacteria, a fungus, a yeast and a parasite. In certain embodiments, a therapeutic composition does not contain a virus.

In some embodiments, a therapeutic composition comprises a modified HAF. In certain embodiments, a modified HAF is a composition that is processed to remove one or more of cells, pathogens, vernix, lanugo and/or macroparticles (e.g., particles greater than 400 nm, greater than 300 nm or greater than 200 nm in diameter). In some embodiments, a modified HAF is substantially or completely free of cells, pathogens, vernix, lanugo and macroparticles. In some embodiments, a modified HAF is substantially free of nanoparticles. In certain embodiments, a modified HAF is a filtered HAF. In some embodiments, a modified HAF is HAF that is filtered through a filter having a pore size of 0.2 um or larger, or 0.1 um or larger. In some embodiments, a modified HAF is HAF that is filtered through a filter having a pore size of 0.1 um to 1 um, 0.2 um to 1 um, or 0.2 um to 0.5 um. In certain embodiments, a modified HAF is HAF that is subjected to centrifugation at 100×g to 2500×g, or 200×g to 2000×g for a suitable period of time.

In some embodiments, a therapeutic composition comprises 0% to 99% (vol/vol) modified HAF. In certain embodiments, a therapeutic composition comprises 50% to 99%, 60%-99%, 70%-99%, 70%-95% or 70%-90% modified HAF.

In some embodiments, a therapeutic composition comprises nanoparticles. In some embodiments, a therapeutic composition comprises HAF-derived nanoparticles. In some embodiments, a therapeutic composition comprises 1% to 50% (vol/vol) nanoparticles. In some embodiments, a therapeutic composition comprises 1% to 40%, 1% to 30%, 1% to 25%, 5% to 40%, 5% to 30%, 5% to 25%, or 10% to 40% (vol/vol) nanoparticles.

In some embodiments, a therapeutic composition comprises at least $1\times10^8$, at least $1\times10^9$, at least $1\times10^{10}$, at least $1\times10^{11}$, at least $2\times10^{11}$, at least $4\times10^{11}$, at least $5\times10^{11}$ or at least $1\times10^{12}$ (particles/ml). In some embodiments, a therapeutic composition comprises a mean, average or absolute amount of nanoparticles in a range of $1\times10^8$ to $1\times10^{20}$ (particles/ml). In some embodiments, a therapeutic composition comprises a mean, average or absolute amount of nanoparticles in a range of $1\times10^8$ to $1\times10^{18}$, $1\times10^9$ to $1\times10^{18}$, $1\times10^{10}$ to $1\times10^{18}$, $1\times10^{11}$ to $1\times10^{18}$, $1\times10^{12}$ to $1\times10^{18}$, $1\times10^{13}$ to $1\times10^{18}$, $1\times10^{14}$ to $1\times10^{18}$, $1\times10^{12}$ to $1\times10^{16}$, $1\times10^{12}$ to $1\times10^{15}$, $1\times10^{12}$ to $1\times10^{15}$, $1\times10^{11}$ to $1\times10^{16}$, $1\times10^{11}$ to $1\times10^{14}$, or $1\times10^{11}$ to $1\times10^{13}$ (particles/ml). In some embodiments, a therapeutic composition comprises a mean, average or absolute amount of nanoparticles in a range of $1\times10^8$ to $1\times10^{13}$ or $1\times10^8$ to $1\times10^{12}$ (particles/ml). In some embodiments, a therapeutic composition comprises a mean, average or absolute amount of nanoparticles in a range of $1\times10^{11}$ to $1\times10^{13}$, $4\times10^{11}$ to $1\times10^{13}$, $5\times10^{11}$ to $1.5\times10^{12}$ or $4\times10^{11}$ to $1.1\times10^{12}$ (particles/ml). In some embodiments, a therapeutic composition comprises a mean, average or absolute amount of nanoparticles in a range of about $4\times10^{11}$ to about $7.5\times10^{11}$ (particles/ml).

In some embodiments, a therapeutic composition comprises hyaluronic acid. In some embodiments, a therapeutic composition comprises an amount of hyaluronic acid of at least 100 ng/ml, at least 200 ng/ml, at least 250 ng/ml, at least 300 ng/ml, at least 350 ng/ml, at least 400 ng/ml, at least 500 ng/ml, at least 550 ng/ml, at least 600 ng/ml or at least 700 ng/ml. In some embodiments, a therapeutic composition comprises a mean, average or absolute amount of hyaluronic acid in a range of 100-5000 ng/ml, 200-5000 ng/ml, 300-5000 ng/ml, 400-5000 ng/ml, 500-5000 ng/ml, 200-3000 ng/ml, 200-2000 ng/ml, 200-1000 ng/ml, 200-500 ng/ml, 300-500, 500-800 ng/ml or 600-800 ng/ml. In some embodiments, a therapeutic composition comprises a hyaluronic acid that is derived from or naturally found in HAF. In some embodiments, a therapeutic composition comprises a hyaluronic acid that is recombinantly produced. In some embodiments, a therapeutic composition comprises a hyaluronic acid that is expressed, produced, isolated and/or purified from a non-human source.

In some embodiments, a therapeutic composition comprises one or more cytokines, soluble receptors and/or growth factors selected from the cytokines, soluble receptors and growth factor shown in FIGS. 4, 5A, 5B, 5C and 6. In some embodiments, a therapeutic composition comprises one or more cytokines, soluble receptors and/or growth factors, non-limiting examples of which include angiogenin (ANG), BLC, EGF (epidermal growth factor), FGF-6 (fibroblast growth factor 6), GCP-2 (CXCL6), IGFBP-1 (Insulin Like Growth Factor Binding Protein 1), IGF-BP2 (Insulin Like Growth Factor Binding Protein 2), IGF-BP4 (Insulin Like Growth Factor Binding Protein 4), IL-1RA (Interleukin 1 Receptor Antagonist), IL-6, LEPTIN, MCP-1 (CCL2), MIG (CXCL9), MIP-1DELTA, NAP-2, adiponectin (ACRP30), GRO-A, HCC-4, HGF, ICAM-1, IGFBP-6, IL-1R4, IL-6R, IL-8, OPG, sTNFRII, sTNFRI, TIMP-1, TIMP-2, and UPAR. In some embodiments, a therapeutic composition comprises two or more cytokines, soluble receptors and/or growth factors selected from the list of angiogenin (ANG), BLC, EGF, FGF-6, GCP-2, IGFBP-1, IGF-BP2, IGF-BP4, IL-1RA, IL-6, LEPTIN, MCP-1, MIG, MIP-1DELTA, NAP-2, adiponectin (ACRP30), GRO-A, HCC-4, HGF, ICAM-1, IGFBP-6, IL-1R4, IL-6R, IL-8, OPG, sTNFRII, sTNFRI, TIMP-1, TIMP-2, and UPAR. In some embodiments, a therapeutic composition comprises one or more, three or more, four or more, five or more, six or more, eight or more or ten or more cytokines, soluble receptors and/or growth factors selected from the list of angiogenin (ANG), BLC, EGF, FGF-6, GCP-2, IGFBP-1, IGF-BP2, IGF-BP4, IL-1RA, IL-6, LEPTIN, MCP-1, MIG, MIP-1DELTA, NAP-2, adiponectin (ACRP30), GRO-A, HCC-4, HGF, ICAM-1, IGFBP-6, IL-1R4, IL-6R, IL-8, OPG, sTNFRII, sTNFRI, TIMP-1, TIMP-2, and UPAR. In some embodiments, a therapeutic composition comprises ANG, IL-1RA, MCP-1, IL-6, UPAR, FGF-6, EGF, HGF, LEPTIN and ACRP30. In some embodiments, a therapeutic composition comprises one or more, three or more, four or more, five or more, six or more, eight or more or ten or more cytokines, soluble receptors and/or growth factors selected from the list of ACRP30, AGRP, ANGPT2, AREG, AXL, B-NGF, BFGF, BTC, CCL28, CTAK, DTK, EGFR, ENA-78, FAS, FGF-4, FGF-9, G-CSF, GITR, GITR LIGAND, GRO, GRO-ALPHA, HCC-4, HGF, I-TAC, ICAM-1, ICAM-3, IGF-1SR, IGFBP-3, IGFBP-6, IL-11, IL-12 P40, IL-12 P70, IL-17, IL-1R1, IL-2R ALPHA, IL-6R, IL-8, IL1R4, MIF, MIP-1 ALPHA, MIP-2 BETA, MIP-3 BETA, MSP ALPHA, NT-4, OPG, OSM, PLGF, SGP130, sTNFRI, sTNFRII, TECK, THPO, TIMP-1, TIMP-2, TRAIL R3, TRAIL R4, UPAR, VEGF, VEGF-D, XCL1, ANG, BDNF, BLC, BMP4, BMP6, CCL23, CNTP, EGF, Eoxtanin 1, Eoxtanin 2, Eoxtaxin 3, FGF-6, FGF-7, FLT3-LIGAND, FRACTALKINE, GCP-2, GDNF, GMCSF, 1-309, IGF-1, IGFBP1, IGFBP2, IGFBP4, IL-10, IL-13, IL-15, IL-16, IL-1B, IL-1RA, IL-2, IL-3, IL-4, IL-5, IL-6, IL-7, IL1-A, IFN GAMMA (IFNγ), LEPTIN, LIGHT, M-CSF, MCP-1, MCP-2, MCP-3, MCP4, MDC, MIG, MIP-1A, MIP-3A, NAP-2, NT-3, PARC, PDGFBB, RANTES, SCF, SDF1A, TARC, TGF-B1, TGF-B3, TNFA and TNFB. In some embodiments, a therapeutic composition comprises a cytokine or growth factor that is derived from or naturally found in HAF. In some embodiments, a therapeutic composition comprises a cytokine or growth factor that is recombinantly produced. In some embodiments, a therapeutic composition comprises a cytokine or growth factor that is expressed, produced, isolated and/or purified from a non-human source.

In some embodiments, a therapeutic composition comprises an amount of a cytokine or a growth factor of at least at least 10 pg/ml, at least 100 pg/ml, at least 1 ng/ml, at least 50 ng/ml, at least 100 ng/ml, at least 200 ng/ml, at least 250 ng/ml, at least 300 ng/ml, at least 400 ng/ml, at least 500 ng/ml, at least 600 ng/ml or at least 700 ng/ml. In some embodiments, a therapeutic composition comprises a mean, average or absolute amount of a cytokine or growth factor in a range of 1-5000 ng/ml, 10-5000 ng/ml, 100-5000 ng/ml, 200-5000 ng/ml, 300-5000 ng/ml, 400-5000 ng/ml or 500-5000 ng/ml.

In some embodiments, a therapeutic composition comprises an amount of CD63 of at least 10 pg/ml, at least 100 pg/ml, at least 200 pg/ml, at least 300 pg/ml, at least 400 pg/ml, at least 500 pg/ml, at least 1 ng/ml, at least 50 ng/ml, at least 100 ng/ml, at least 200 ng/ml, at least 250 ng/ml, at least 300 ng/ml, at least 400 ng/ml, at least 500 ng/ml, at least 600 ng/ml or at least 700 ng/ml. In some embodiments, a therapeutic composition comprises a mean, average or absolute amount of CD63 in a range of 100 pg/ml-1000 ng/ml, 300 pg/ml-1000 ng/ml, 400 pg/ml-1000 ng/ml or 450 pg/ml-1000 ng/ml.

Nanoparticles

In some embodiments, a therapeutic composition comprises nanoparticles (e.g., a plurality of nanoparticles). In some embodiments, a therapeutic composition comprises or consists of HAF derived nanoparticles (e.g., a plurality of nanoparticles). In some embodiments, nanoparticles comprise or consists of exosomes. In some embodiments, nanoparticles comprise or consists of endosomes. In some embodiments, a nanoparticle or exosome comprises a membrane bound or membrane encapsulated vesicle. In some embodiments, a nanoparticle comprises a membrane bound or membrane encapsulated vesicle where the membrane component comprises a phospholipid bilayer. In some embodiments, a nanoparticle is derived from HAF. In some embodiments, a nanoparticle is a synthetic membrane encapsulated vesicle that can be loaded with a membrane-bound or intra-vesicular cargo of choice.

As disclosed herein, nanoparticles or exosomes derived from HAF differ from exosomes derived from other sources. HAF derived exosomes differ in their miRNA content, as well as their protein content from exosomes found in other bodily fluids, such as milk, blood, urine. Without being limited to theory, the exosomes derived from HAF are unique because they are derived and or produced from maternal, fetal, and placental tissues, and the many different cell types that are in contact with amniotic fluid.

In some embodiments, nanoparticles have a mean, average or absolute diameter of at least 10 nm, at least 25 nm, at least 40 nm, at least 50 nm, at least 55 nm, at least 60 nm, at least 70 nm, at least 80 nm, at least 90 nm or at least 100 nm. In some embodiments, nanoparticles have a mean, average or absolute diameter of at least 50 nm. In some embodiments, nanoparticles have a mean, average or absolute diameter in a range of about 10 nm to 300 nm, 30 nm to 300 nm, 40 nm to 300 nm, 50 nm to 300 nm, 50 nm to 250 nm, 50 nm to 250 nm, 50 nm to 200 nm, 75 nm to 200 nm, or 100 nm to 150 nm. In some embodiments, nanoparticles have a mean, average or absolute diameter in a range of about 100 to 200 nm. In some embodiments, nanoparticles have a mean, average or absolute diameter of about 100 nm, 125 nm, 150 nm, 175 nm or about 200 nm.

In some embodiments, a nanoparticle comprises one or more surface bound proteins, non-limiting examples of which include CD9, CD63, CD81, CD326, CD133, CD14, CD24, CD42a, CD44, CD29, CD146, HLA-DR, HLA-DP and HLA-DQ. In some embodiments, a nanoparticle comprises two or more, five or more, or ten or more surface bound proteins selected from CD9, CD63, CD81, CD326, CD133, CD14, CD24, CD42a, CD44, CD29, CD146, HLA-DR, HLA-DP and HLA-DQ. In some embodiments, a nanoparticle comprises three or more surface-bound proteins selected from the group consisting of CD9, CD63, CD81, CD326 and CD133. In some embodiments, a nanoparticle comprises two or more surface-bound proteins selected from CD14, CD24, CD42a, CD44, CD29, CD14 and CD146. In some embodiments, a nanoparticle comprises surface-bound CD9, CD63, CD81, CD326 and CD133. In some embodiments, a nanoparticle comprises surface-bound CD14, CD24, CD42a, CD44, CD29, CD14 and CD146. In some embodiments, a nanoparticle comprises surface-bound HLA-DR, HLA-DP and HLA-DQ. In some embodiments, a nanoparticle comprises surface-bound CD63.

In some embodiments, a nanoparticle comprises one or more microRNAs (miRNAs). In certain embodiments, an miRNA is a small non-coding RNA molecule, sometimes containing about 22 nucleotides, that often functions in RNA silencing and post-transcriptional regulation of gene expression. In some embodiments, a nanoparticle comprises one or more miRNAs selected from Table 1. In some embodiments, a nanoparticle comprises two, three, four, five, ten, twenty, twenty five or thirty or more miRNAs selected from Table 1. In some embodiments, a nanoparticle comprises five or more miRNAs selected from hsa-let-7b, hsa-mir-200c, hsa-mir-30d, hsa-mir-125a, hsa-mir-483, hsa-mir-34c, hsa-mir-200a, hsa-mir-148a, hsa-mir-191, hsa-mir-21, hsa-mir-146a, hsa-mir-26b, hsa-mir-92b, hsa-mir-342, hsa-mir-34b, hsa-mir-423, hsa-mir-205, hsa-mir-203a, hsa-mir-99b, hsa-mir-375, hsa-mir-10b, hsa-mir-449c, hsa-mir-320a and hsa-let-7f-2. In some embodiments, a nanoparticle comprises five or more, or ten or more miRNAs selected from hsa-let-7b, hsa-mir-200c, hsa-mir-30d, hsa-mir-125a, hsa-mir-483, hsa-mir-34c, hsa-mir-200a, hsa-mir-148a, hsa-mir-191, hsa-mir-21, hsa-mir-146a, hsa-mir-26b, hsa-mir-92b, hsa-mir-342, hsa-mir-34b, hsa-mir-423, hsa-mir-205, hsa-mir-203a, hsa-mir-99b, hsa-mir-375, hsa-mir-10b, hsa-mir-449c, hsa-mir-320a, hsa-let-7f-2, hsa-mir-23a, hsa-mir-27b, hsa-mir-93, hsa-mir-221, hsa-mir-425, hsa-mir-151a, hsa-mir-190b, hsa-mir-223, hsa-mir-1180, hsa-mir-184, hsa-mir-361, hsa-mir-182, hsa-mir-92a-1, hsa-mir-29a, hsa-mir-183, hsa-mir-204, hsa-mir-574, hsa-mir-532, hsa-mir-28, hsa-mir-744, hsa-mir-2110, hsa-mir-140, hsa-mir-1307, hsa-mir-193b, hsa-mir-660, hsa-mir-224, hsa-mir-196b, hsa-mir-339, hsa-mir-186, hsa-mir-3065, hsa-mir-378a, hsa-mir-16-1, hsa-mir-338, hsa-mir-126, hsa-mir-95, hsa-mir-142, hsa-mir-328, hsa-mir-335, hsa-mir-125b-2, hsa-mir-149 and hsa-mir-150. In some embodiments, a nanoparticle comprises two or more miRNAs selected from hsa-mir-30d, hsa-mir-191, hsa-mir-21 and hsa-mir-146a. In some embodiments, a nanoparticle comprises hsa-mir-30d, hsa-mir-191, hsa-mir-21 and hsa-mir-146a.

In some embodiments, a nanoparticle comprises one or more soluble proteins, non-limiting examples of which include enzymes, hormones, cytokines and growth factors. In some embodiments, a nanoparticle comprises one or more of DNA polymerase beta, DNA polymerase lambda, telomerase reverse transcriptase and RAD50. In some embodiments, a nanoparticle comprises DNA polymerase beta, DNA polymerase lambda, telomerase reverse transcriptase and RAD50.

Methods

Presented herein, in certain embodiments, are methods of treating, preventing, or delaying the onset of a disease or disorder, or inhibiting, delaying the onset of, reducing the severity of, or ameliorating one or more symptoms or secondary complications of a disease or disorder disclosed herein, where the method comprises administering a composition disclosed herein to a subject in need thereof. In some embodiments, a method of treating or preventing a disease or disorder in a subject in need thereof, comprising administering to the subject a therapeutically effective amount of the therapeutic composition or pharmaceutical composition disclosed herein.

In some embodiments, a disease or disorder comprises a lung disease or a lung disorder, selected from acute respiratory syndrome, chronic obstructive pulmonary disease (COPD), and bronchopulmonary dysplasia (BPD). In some embodiments, a lung disease or a lung disorder comprises acute respiratory syndrome (e.g., a sudden acute respiratory syndrome). In some embodiments, a lung disease or a lung disorder comprises or consists of acute respiratory syndrome induced by a coronavirus infection. In some embodiments, a lung disease or a lung disorder comprises or consists of acute respiratory syndrome induced by a COVID19 infection or a SARS-associated coronavirus (SARS-CoV) infection. In certain embodiments, a method comprises preventing, delaying the onset of, reducing the severity of, or ameliorating one or more symptoms or secondary complication of bronchopulmonary dysplasia (BPD). A secondary complication of BPD may include pulmonary hypertension or heart dysfunction. Accordingly, in certain embodiments a method comprises preventing, delaying the onset of, reducing the severity of, or ameliorating pulmonary hypertension or heart dysfunction in a subject having, diagnosed with or suspected of having bronchopulmonary dysplasia (BPD).

In certain embodiments, a method comprises treating, preventing, or delaying the onset of arthritis, or chronic or acute inflammation of the joints. In certain embodiments, a method comprises inhibiting, delaying the onset of, reducing the severity of, or ameliorating one or more symptoms of arthritis, or chronic or acute inflammation of the joints. In some embodiments, an arthritis is osteoarthritis or rheumatoid arthritis.

Subjects

The term "subject" refers to a mammal. Any suitable mammal can be treated by a method or composition described herein. Non-limiting examples of mammals include a human, non-human primate (e.g., ape, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In some embodiments a subject is a non-human primate or a human. In some embodiments a subject is a human. A subject can be any age or at any stage of development (e.g., an adult, teen, child, infant, or a mammal in utero). A subject can be male or female.

In some embodiments, a subject is a subject infected with a coronavirus. In some embodiments, a subject is a subject infected with COVID19 or SARS-associated coronavirus (SARS-CoV).

Pharmaceutical Compositions

In some embodiments, a pharmaceutical composition comprises a therapeutic composition described herein. In some embodiments, a pharmaceutical composition comprises a therapeutically effective amount of a therapeutic composition described herein. In some embodiments a pharmaceutical composition comprising a therapeutic composition described herein for use in treating or preventing a disease or disorder in a subject, or one or more symptoms thereof. In some embodiments, a pharmaceutical composition comprises a therapeutic composition described herein and a pharmaceutically acceptable excipient, diluent, additive or carrier.

A pharmaceutical composition can be formulated for a suitable route of administration. In some embodiments a pharmaceutical composition is formulated for oral, subcutaneous (s.c.), intradermal, intramuscular, intratracheal, intraarticular, intraperitoneal and/or intravenous (i.v.) administration. In certain embodiments, a pharmaceutical composition contains formulation materials for modifying, maintaining, or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates (e.g., phosphate buffered saline) or suitable organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); solvents (such as glycerin, propylene glycol or polyethylene glycol); diluents; excipients and/or pharmaceutical adjuvants. In particular, a pharmaceutical composition can comprise any suitable carrier, formulation, or ingredient, the like or combinations thereof as listed in "Remington: The Science And Practice Of Pharmacy" Mack Publishing Co., Easton, PA, 19$^{th}$ Edition, (1995)(hereafter, Remington '95), or "Remington: The Science And Practice Of Pharmacy", Pharmaceutical Press, Easton, PA, 22$^{nd}$ Edition, (2013)(hereafter, Remington 2013), the contents of which are incorporated herein by reference in their entirety.

In certain embodiments, a pharmaceutical composition comprises a suitable excipient, non-limiting examples of which include anti-adherents (e.g., magnesium stearate), a binder, fillers, monosaccharides, disaccharides, other carbohydrates (e.g., glucose, mannose or dextrin), sugar alcohols (e.g., mannitol or sorbitol), coatings (e.g., cellulose, hydroxypropyl methylcellulose (HPMC), microcrystalline cellulose, synthetic polymers, shellac, gelatin, corn protein zein, enterics or other polysaccharides), starch (e.g., potato, maize or wheat starch), silica, colors, disintegrants, flavors, lubricants, preservatives, sorbents, sweeteners, vehicles, suspending agents, surfactants and/or wetting agents (such as pluronics, PEG, sorbitan esters, polysorbates such as polysorbate 20, polysorbate 80, triton, tromethamine, lecithin, cholesterol, tyloxapal), stability enhancing agents (such as sucrose or sorbitol), and tonicity enhancing agents (such as alkali metal halides, sodium or potassium chloride, mannitol, sorbitol), and/or any excipient disclosed in Remington '95 or Remington 2013. The term "binder" as used herein refers to a compound or ingredient that helps keep a pharmaceutical mixture combined. Suitable binders for making pharmaceutical formulations and are often used in the preparation of pharmaceutical tablets, capsules and granules.

In some embodiments a pharmaceutical composition comprises a suitable pharmaceutically acceptable additive and/or carrier. Non-limiting examples of suitable additives include a suitable pH adjuster, a soothing agent, a buffer, a sulfur-containing reducing agent, an antioxidant and the like. Non-limiting examples of a sulfur-containing reducing agent include those having a sulfhydryl group (e.g., a thiol) such as N-acetylcysteine, N-acetylhomocysteine, thioctic acid, thiodiglycol, thioethanolamine, thioglycerol, thiosorbitol, thioglycolic acid and a salt thereof, sodium thiosulfate, glutathione, and a C1-C7 thioalkanoic acid. Non-limiting examples of an antioxidant include erythorbic acid, dibutylhydroxytoluene, butylhydroxyanisole, alpha-tocopherol, tocopherol acetate, L-ascorbic acid and a salt thereof, L-ascorbyl palmitate, L-ascorbyl stearate, sodium bisulfite, sodium sulfite, triamyl gallate and propyl gallate, as well as chelating agents such as disodium ethylenediaminetetraacetate (EDTA), sodium pyrophosphate and sodium metaphosphate. Furthermore, diluents, additives and excipients may comprise other commonly used ingredients, for example, inorganic salts such as sodium chloride, potassium chloride, calcium chloride, sodium phosphate, potassium phosphate and sodium bicarbonate, as well as organic salts such as sodium citrate, potassium citrate and sodium acetate.

The pharmaceutical compositions used herein can be stable over an extended period of time, for example on the order of months or years. In some embodiments a pharmaceutical composition comprises one or more suitable preservatives. Non-limiting examples of preservatives include benzalkonium chloride, benzoic acid, salicylic acid, thimerosal, phenethyl alcohol, methylparaben, propylparaben, chlorhexidine, sorbic acid, hydrogen peroxide, the like and/or combinations thereof. A preservative can comprise a quaternary ammonium compound, such as benzalkonium chloride, benzoxonium chloride, benzethonium chloride, cetrimide, sepazonium chloride, cetylpyridinium chloride, or domiphen bromide (BRADOSOL®). A preservative can comprise an alkyl-mercury salt of thiosalicylic acid, such as thimerosal, phenylmercuric nitrate, phenylmercuric acetate or phenylmercuric borate. A preservative can comprise a paraben, such as methylparaben or propylparaben. A preservative can comprise an alcohol, such as chlorobutanol, benzyl alcohol or phenyl ethyl alcohol. A preservative can comprise a biguanide derivative, such as chlorhexidine or polyhexamethylene biguanide. A preservative can comprise sodium perborate, imidazolidinyl urea, and/or sorbic acid. A preservative can comprise stabilized oxychloro complexes, such as known and commercially available under the trade name PURITE®. A preservative can comprise polyglycol-polyamine condensation resins, such as known and commercially available under the trade name POLYQUART® from Henkel KGaA. A preservative can comprise stabilized hydrogen peroxide. A preservative can be benzalkonium chloride. In some embodiments a pharmaceutical composition is free of preservatives.

In some embodiments a therapeutic composition or pharmaceutical composition described herein is substantially free of contaminants (e.g., cells, blood cells, platelets, polypeptides, minerals, blood-borne compounds or chemicals, virus, bacteria, fungus, yeast, pathogens, toxins, parasites and the like). In certain embodiments a therapeutic composition or pharmaceutical composition described herein is substantially free of lanugo and/or vernix.

In some embodiments a therapeutic composition or pharmaceutical composition described herein is substantially free of endotoxin. In some embodiments a therapeutic composition or pharmaceutical composition described herein comprises less than 5 EU/ml, less than 2.5 EU/ml, less than 1 EU/ml, less than 0.5 EU/ml, less than 0.1 EU/ml or less than 0.05 EU/ml of endotoxin. In some embodiments a therapeutic composition or pharmaceutical composition described herein is sterile or aseptic.

The pharmaceutical compositions described herein may be configured for administration to a subject in any suitable form and/or amount according to the therapy in which they are employed. For example, a pharmaceutical composition configured for parenteral administration (e.g., by injection or infusion), may take the form of a suspension, solution or emulsion in an oily or aqueous vehicle and it may contain formulation agents, excipients, additives and/or diluents such as aqueous or non-aqueous solvents, co-solvents, suspending solutions, preservatives, stabilizing agents and or dispersing agents. In some embodiments a pharmaceutical composition suitable for parenteral administration may contain one or more excipients. In some embodiments a pharmaceutical composition is lyophilized to a dry powder form. In some embodiments a pharmaceutical composition is lyophilized to a dry powder form, which is suitable for reconstitution with a suitable pharmaceutical solvent (e.g., water, saline, an isotonic buffer solution (e.g., PBS), DMSO, combinations thereof and the like). In certain embodiments, reconstituted forms of a lyophilized pharmaceutical composition are suitable for parenteral administration (e.g., intravenous administration) to a mammal.

In certain embodiments, a pharmaceutical composition is configured for oral administration and may be formulated as a tablet, microtablet, minitablets, micropellets, powder, granules, capsules (e.g., capsules filled with microtablets, micropellets, powders or granules), emulsions, solutions, the like or combinations thereof. Pharmaceutical compositions configured for oral administration may comprise suitable coatings to delay or sustain release of the active ingredient, non-limiting examples of which include enteric coatings such as fatty acids, waxes, shellac, plastics, methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, cellulose acetate trimellitate, sodium alginate, zein, plant fibers, the like and combinations thereof.

In some embodiments a pharmaceutical composition described herein may be configured for topical administration and may include one or more of a binding and/or lubricating agent, polymeric glycols, gelatins, cocoa-butter or other suitable waxes or fats. In some embodiments a pharmaceutical composition described herein is incorporated into a topical formulation containing a topical carrier that is generally suited to topical drug administration and comprising any suitable material known to those skilled in the art. In certain embodiments, a topical formulation of a pharmaceutical composition is formulated for administration of a therapeutic composition described herein from a topical patch.

In certain embodiments, an optimal pharmaceutical composition is determined by one skilled in the art depending upon, for example, on the intended route of administration, delivery format and desired dosage (see e.g., Remington '95 or Remington 2013, supra). A pharmaceutical composition can be manufactured by any suitable manner, including, e.g., by means of conventional mixing, dissolving, granulating, dragee-making, levigating, emulsifying, encapsulating, entrapping or tableting processes (e.g., see methods described in Remington '95 or Remington 2013).

Route of Administration

Any suitable method of administering a therapeutic composition or pharmaceutical composition described herein to a subject can be used. Any suitable formulation and/or route of administration can be used for administration of a therapeutic composition or pharmaceutical composition described herein (e.g., see Fingl et al. 1975, in "The Pharmacological Basis of Therapeutics", which is incorporated herein by reference in its entirety). A suitable formulation and/or route of administration can be chosen by a medical professional (e.g., a physician) in view of, for example, a subject's disorder, disease, risk, age, and/or health condition. Non-limiting examples of routes of administration include topical or local (e.g., transdermally or cutaneously, (e.g., on the skin or epidermis), in or on the eye, intranasally, transmucosally, in the ear, inside the ear (e.g., behind the ear drum)), enteral (e.g., delivered through the gastrointestinal tract, e.g., orally (e.g., as a tablet, capsule, granule, liquid, emulsification, lozenge, or combination thereof), sublingual, by gastric feeding tube, rectally, and the like), by parenteral administration (e.g., parenterally, e.g., intravenously, intraarterially, intramuscularly, intraperitoneally, intradermally, subcutaneously, intracavity, intracranial, intra-articular, into a joint space, intracardiac (into the heart), intracavernous injection, intralesional (into a skin lesion), intraosseous infusion (into the bone marrow), intrathecal (into the spinal canal), intrauterine, intravaginal, intravesical infusion, intravitreal), the like and combinations thereof.

In some embodiments a therapeutic composition described herein or pharmaceutical composition described herein is administered to the lungs, bronchial passages, trachea, esophagus, sinuses, or nasal passages using a suitable method, non-limiting examples of which include intranasal administration, intratracheal instillation, and oral inhalative administration (e.g., by use of an inhaler, e.g., single-/multiple dose dry powder inhalers, nebulizers, and the like).

In some embodiments a therapeutic composition or a pharmaceutical composition disclosed herein is provided to a subject. For example, a composition that is provided to a subject is sometimes provided to a subject for self-administration or for administration to a subject by another (e.g., a non-medical professional). As another example, a composition can be provided as an instruction written by a medical practitioner that authorizes a patient to be provided a composition or treatment described herein (e.g., a prescription). In yet another example, a composition can be provided to a subject where the subject self-administers a composition orally, intravenously or by way of an inhaler, for example.

Alternately, one can administer a composition described herein in a local rather than systemic manner, for example, via direct application to the skin, mucous membrane or region of interest for treating, including using a depot or sustained release formulation.

In certain embodiments a pharmaceutical composition comprising a composition described herein is administered alone (e.g., as a single active ingredient (AI or e.g., as a single active pharmaceutical ingredient (API)). In other embodiments, a pharmaceutical composition comprising a therapeutic composition described herein is administered in combination with one or more additional AIs/APIs, for example, as two separate compositions or as a single composition where the one or more additional AIs/APIs are mixed or formulated together with a therapeutic or pharmaceutical composition described herein.

Dose and Therapeutically Effective Amount

In some embodiments, an amount of a therapeutic or pharmaceutical composition described herein is a therapeutically effective amount. In some embodiments, a therapeutically effective amount of a therapeutic or pharmaceutical composition described herein is administered to a subject. In some embodiments, a therapeutically effective amount of a therapeutic or pharmaceutical composition described herein is an amount needed to obtain an effective therapeutic outcome. In certain embodiments, a therapeutically effective amount is an amount sufficient to prevent, treat, reduce the severity of, delay the onset of, and/or inhibit, reduce or alleviate one or more symptoms or secondary complications of a lung disease or lung disorder selected from acute respiratory syndrome (e.g., an acute respiratory syndrome induced by a coronavirus infection), chronic obstructive pulmonary disease (COPD) and bronchopulmonary dysplasia. In certain embodiments, a therapeutically effective amount is an amount sufficient to prevent, treat, reduce the severity of, delay the onset of, and/or inhibit, reduce or alleviate one or more symptoms of arthritis (e.g., osteoarthritis or rheumatoid arthritis). Determination of a therapeutically effective amount is well within the capability of those skilled in the art, especially in light of the detailed disclosure provided herein.

In certain embodiments, a therapeutically effective amount is an amount high enough to provide an effective therapeutic effect (e.g., a beneficial therapeutic effect) and an amount low enough to minimize unwanted adverse reactions. Accordingly, in certain embodiments, a therapeutically effective amount of a therapeutic composition described herein may vary from subject to subject, often depending on age, weight, general health condition of a subject, severity of a condition being treated, and/or a particular combination of drugs administered to a subject. Thus, in some embodiments, a therapeutically effective amount is determined empirically. Accordingly, a therapeutically effective amount of a therapeutic composition described herein that is administered to a subject can be determined by one of ordinary skill in the art based on amounts found effective in animal or clinical studies, a physician's experience, and suggested dose ranges or dosing guidelines, for example.

In certain embodiments, a therapeutically effective amount of a composition described herein (e.g., a therapeutic or pharmaceutical composition) is administered at a suitable dose (e.g., at a suitable volume, frequency and/or concentration, which often depends on a subject's weight, age and/or condition) intended to obtain an acceptable therapeutic outcome. In certain embodiments, a therapeutically effective amount of a therapeutic composition described herein comprises one or more doses selected from at least 0.001 mg/kg (e.g., mg of total protein of a composition described herein per kg body weight of a subject), at least 0.01 mg/kg, at least 0.1 mg/kg, at least 1 mg/kg, at least 10 mg/kg or at least 100 mg/kg. In certain embodiments, a therapeutically effective amount of a composition described herein is selected from one or more doses of about 0.001 mg/kg (e.g., mg of a therapeutic composition described herein per kg body weight of a subject) to about 5000 mg/kg, 0.01 mg/kg to 1000 mg/kg, 0.01 mg/kg to 500 mg/kg, 0.1 mg/kg to 1000 mg/kg, 1 mg/kg to 1000 mg/kg, 10 mg/kg to 1000 mg/kg, 100 mg/kg to 1000 mg/kg, 0.1 mg/kg to 500 mg/kg, 0.1 mg/kg to 250 mg/kg, 0.1 mg/kg to 150 mg/kg, 0.1 mg/kg to 100 mg/kg, 0.1 mg/kg to 75 mg/kg, 0.1 mg/kg to 50 mg/kg, 0.1 mg/kg to 25 mg/kg, 0.1 mg/kg to 10 mg/kg, 0.1 mg/kg to 5 mg/kg, and 0.5 mg/kg to 5 mg/kg, intervening amounts and combinations thereof. In some aspects a therapeutically effective amount of a composition described herein that is administered to a subject comprises one or more doses of about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 50 mg/kg, 100 mg/kg, 500 mg/kg, and intervening amounts and combinations thereof. In some embodiments a therapeutically effective amount of a therapeutic composition described herein is between about 0.1 mg/kg and about 50 mg/kg.

In certain embodiments, the amount of nanoparticles in a therapeutic or pharmaceutical composition is determined. Accordingly, in some embodiments, a therapeutically effective amount of a composition described herein (e.g., a therapeutic or pharmaceutical composition) is administered as a suitable dose of nanoparticles intended to obtain an acceptable therapeutic outcome. In certain embodiments, a therapeutically effective amount of a composition described herein comprises one or more doses selected from at least $1.1 \times 10^8$ particles/kg (e.g., per kg body weight of a subject), at least $1.1 \times 10^9$ particles/kg, at least $1.1 \times 10^{10}$ particles/kg, at least $1.1 \times 10^{11}$ particles/kg, at least $1.1 \times 10^{12}$ particles/kg or at least $1.1 \times 10^{13}$ particles/kg. In certain embodiments, a therapeutically effective amount of a composition described herein is selected from one or more doses in a range of about $1.1 \times 10^8$ particles/kg (e.g., per kg body weight of a subject) to about $1.1 \times 10^{18}$ particles/kg, $1.1 \times 10^8$ particles/kg to $1.1 \times 10^{16}$ particles/kg, $1.1 \times 10^8$ particles/kg to $1.1 \times 10^{12}$ particles/kg, intervening amounts and combinations thereof.

In some embodiments administering a therapeutically effective amount of a composition described herein comprises administering a suitable dose at a frequency or interval as needed to obtain an effective therapeutic outcome. In some embodiments administering a therapeutically effective amount of a composition described herein comprises administering a suitable dose hourly, every two hours, every 4 hours, every 6 hours, three times a day, twice a day, once a day, six times a week, five times a week, four times a week, three times a week, twice a week, weekly, monthly, quarterly, biannually, annually at combinations thereof, and/or at regular or irregular intervals thereof, and/or simply at a frequency or interval as needed or recommended by a medical professional. In some embodiments, a therapeutically effective amount of a composition described herein is administered continuously by, for example by intravenous administration.

Kits

In some embodiments, provided herein is a kit comprising a therapeutic composition or a pharmaceutical composition (i.e., a composition) described herein. In some embodiments, a kit comprises one or more doses of a composition described herein. In some embodiments, a kit comprises one or more packs and/or one or more dispensing devices, which can contain one or more doses of a composition described herein. Non-limiting examples of a pack include a metal, glass, or plastic container, syringe or blister pack that comprises a suitable amount or dose of a composition described herein. In certain embodiments, a kit comprises a dispensing device such as a syringe or inhaler, that may or may not comprise a composition described herein. A pack and/or dispenser device can be accompanied by instructions for administration. The pack or dispenser can also be accompanied with a notice associated with the container in a form prescribed by a governmental agency regulating the manufacture, use, or sale of a pharmaceuticals, which notice is reflective of approval by the agency of the form of the drug for human or veterinary administration. Such notice, for example, can be the labeling approved by the U.S. Food and Drug Administration for prescription drugs, or the approved product insert.

In some embodiments a kit or pack comprises an amount of a composition described herein sufficient to treat a patient for 1 day to 1 year, 1 day to 180 days, 1 day to 120 days, 1 day to 90 days, 1 day to 60 days, 1 day to 30 days, 1-24 hours, 1-12 hours, 1-4 hours, or amount of time there between.

A kit optionally includes a product label and/or one or more packaging inserts, that provide a description of the components or instructions for use in vitro, in vivo, or ex vivo, of the components therein. Exemplary instructions may include instructions for a treatment protocol or therapeutic regimen. In certain embodiments, a kit comprises packaging material, which refers to a physical structure housing components of the kit. The packaging material can maintain the components sterilely and can be made of material commonly used for such purposes (e.g., paper, corrugated fiber, glass, plastic, foil, ampules, vials, tubes, etc.). Product labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, optical disk such as CD- or DVD-ROM/RAM, DVD, MP3, magnetic tape, or an electrical storage media such as RAM and ROM or hybrids of these such as magnetic/optical storage media, FLASH media or memory-type cards. Product labels or inserts can include identifying information of one or more components therein, dose amounts, clinical pharmacology of the active ingredient(s) including mechanism of action, pharmacokinetics (PK) and pharmacodynamics (PD). Product labels or inserts can include information identifying manufacturer information, lot numbers, manufacturer location, date, information on an indicated condition, disorder, disease or symptom for which a kit component may be used. Product labels or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimes set forth herein. A kit can additionally include labels or instructions for practicing any of the methods described herein. Product labels or inserts can include information on potential adverse side effects and/or warnings.

EXAMPLES

Example 1—Manufacturing

Organicell Flow is an acellular therapeutic composition derived from human amniotic fluid (HAF). Organicell Flow was prepared by aseptically collecting amniotic fluid from screened and qualified donors. Once obtained, the HAF was centrifuged at 500×g for 10 minutes (min.) and 2000×g for 30 min at 4° C. to remove large cell debris. After centrifugation, the supernatant was transferred into a new vial and filtered with a 0.22 uM filter while preserving sterility.

Organicell Flow XL is also an acellular therapeutic composition derived from human amniotic fluid (HAF). Organicell Flow XL was prepared by aseptically collecting amniotic fluid from screened and qualified donors. Once obtained, the HAF was centrifuged at 500×g for 10 minutes at 4° C. The sample supernatant was then transferred to sterile conical tubes. The sample pellet was discarded. The fluid was then centrifuged at 2000×g for 30 minutes at 4° C. The sample supernatant was collected. A portion of the processed HAF (~¼) was set aside for later exosome resuspension. Another portion of the processed HAF (~¾) was used for exosome isolation. Another portion of the processed HAF was used for the "Control" sample. The filtered fluid was subjected to ultracentrifugation at 100,000×g for a minimum of 3 hours to pellet the exosome fraction. Each exosome pellet was resuspended with the processed HAF set aside for re-suspension. The resuspended exosomes were transferred into the total volume of HAF set aside for resuspension. This process was repeated until all exosome pellets were resuspended and transferred to the HAF set aside for resuspension. After resuspension was complete, the solution was subjected to filtration using a 0.22 uM filter. Filtered product was then aliquoted.

Figure 1B:
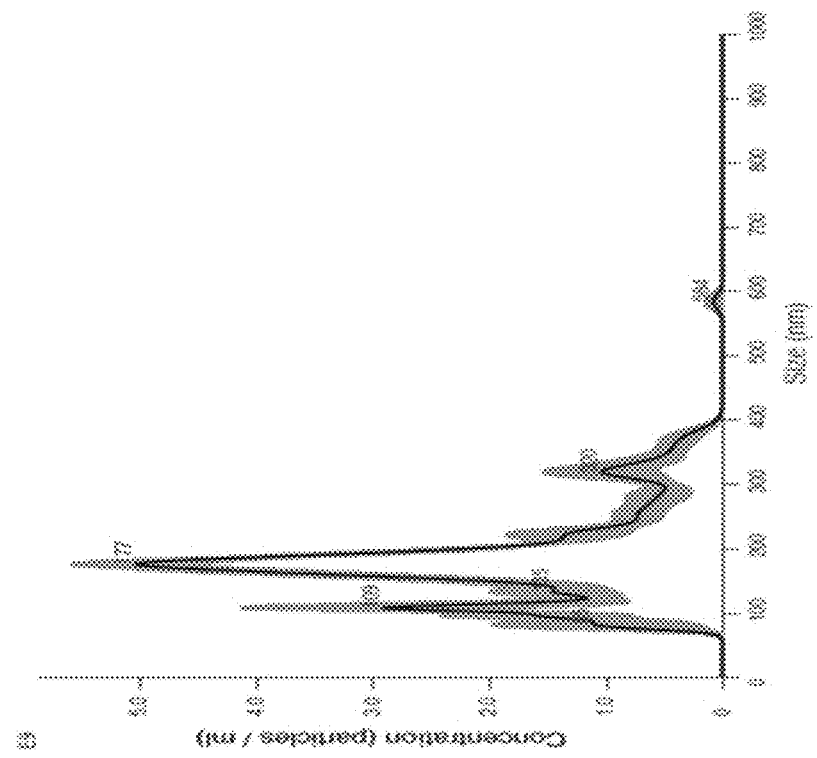
Figure 1C:
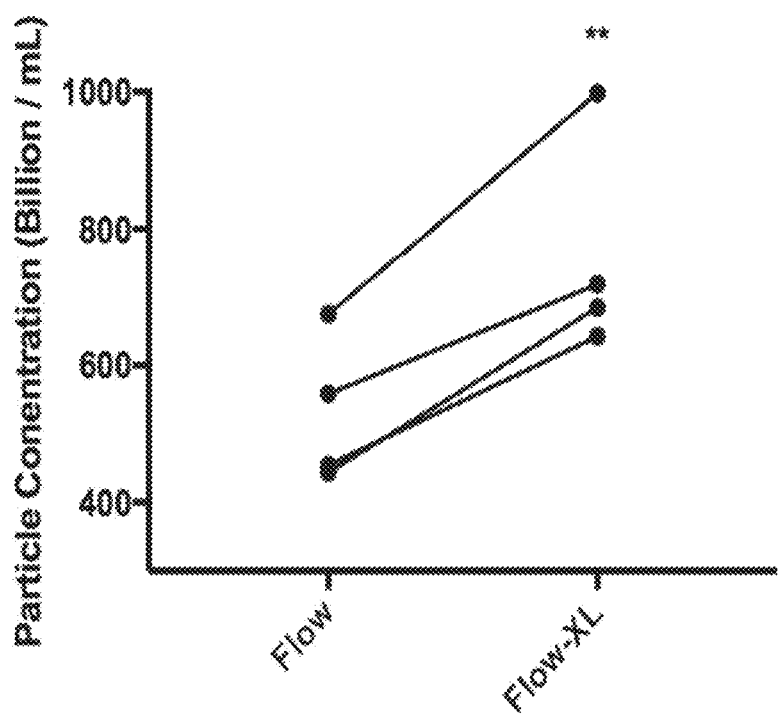
Figure 2:
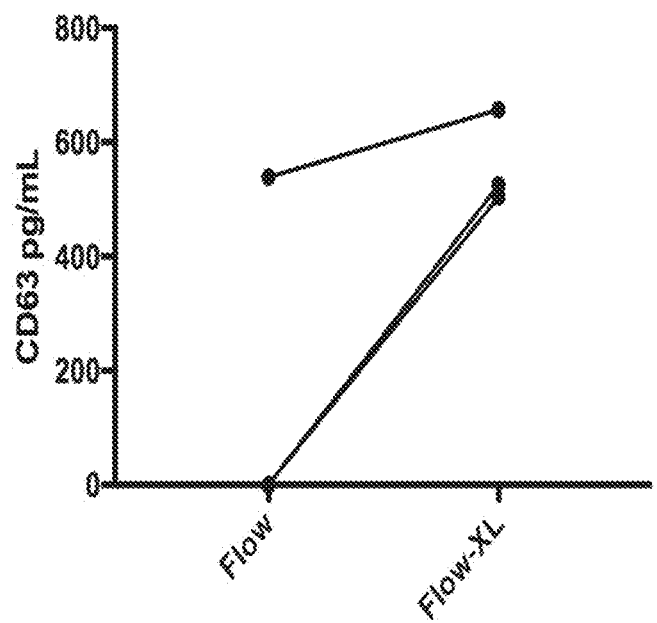
FIG. 2 shows a concentration determination of exosome marker CD63 in Organicell Flow (Flow) and Organicell Flow-XL (Flow-XL). The y-axis shows the concentration of CD63 (pg/ml). Connection lines with a positive slope are representative of increased CD63 concentration between Flow-XL and Flow (N=3).

Successful production of Flow-XL was confirmed by Nanosight Nanoparticle analysis (FIG. 1) and exosome marker quantification by ELISA (FIG. 2). Using Nanosight NS300, the nanoparticle distribution of Organicell Flow (FIG. 1A) was compared to Organicell Flow-XL (FIG. 1B). The analysis demonstrated a significant increased nanoparticle concentration in Flow-XL products compared to the Flow Control (FIG. 1C). An increased concentration of exosome marker CD63 in the Flow-XL products was also demonstrated by ELISA (FIG. 2). The Flow-XL manufacturing process was able to elevate CD63 concentrations from undetectable levels to over 400 pg/mL.

Figure 3:
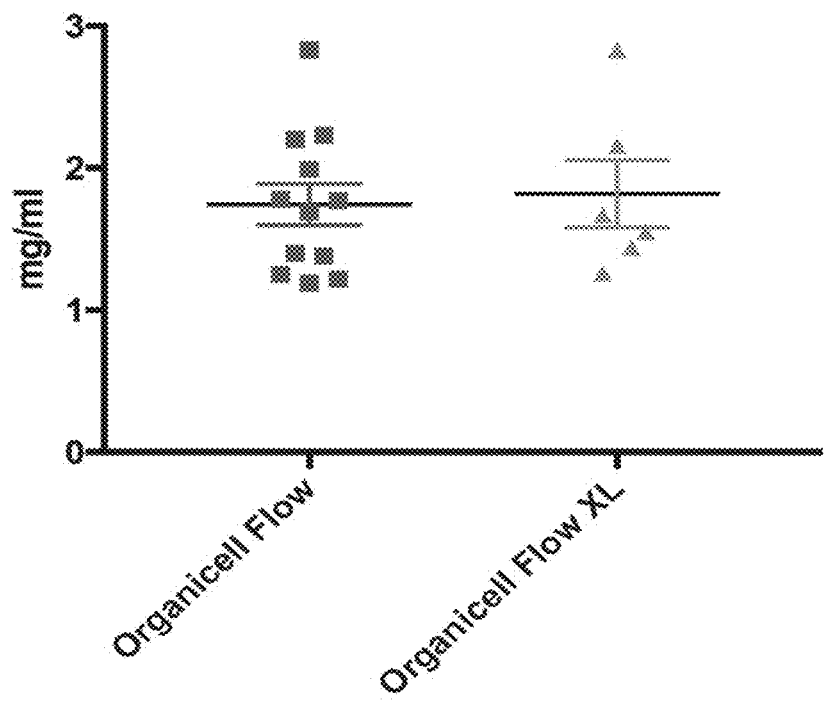
FIG. 3 shows the results of a Bradford analysis of Organicell Flow & Organicell Flow XL products (n=11 for Flow, n=6 for Flow XL).
Figure 4:
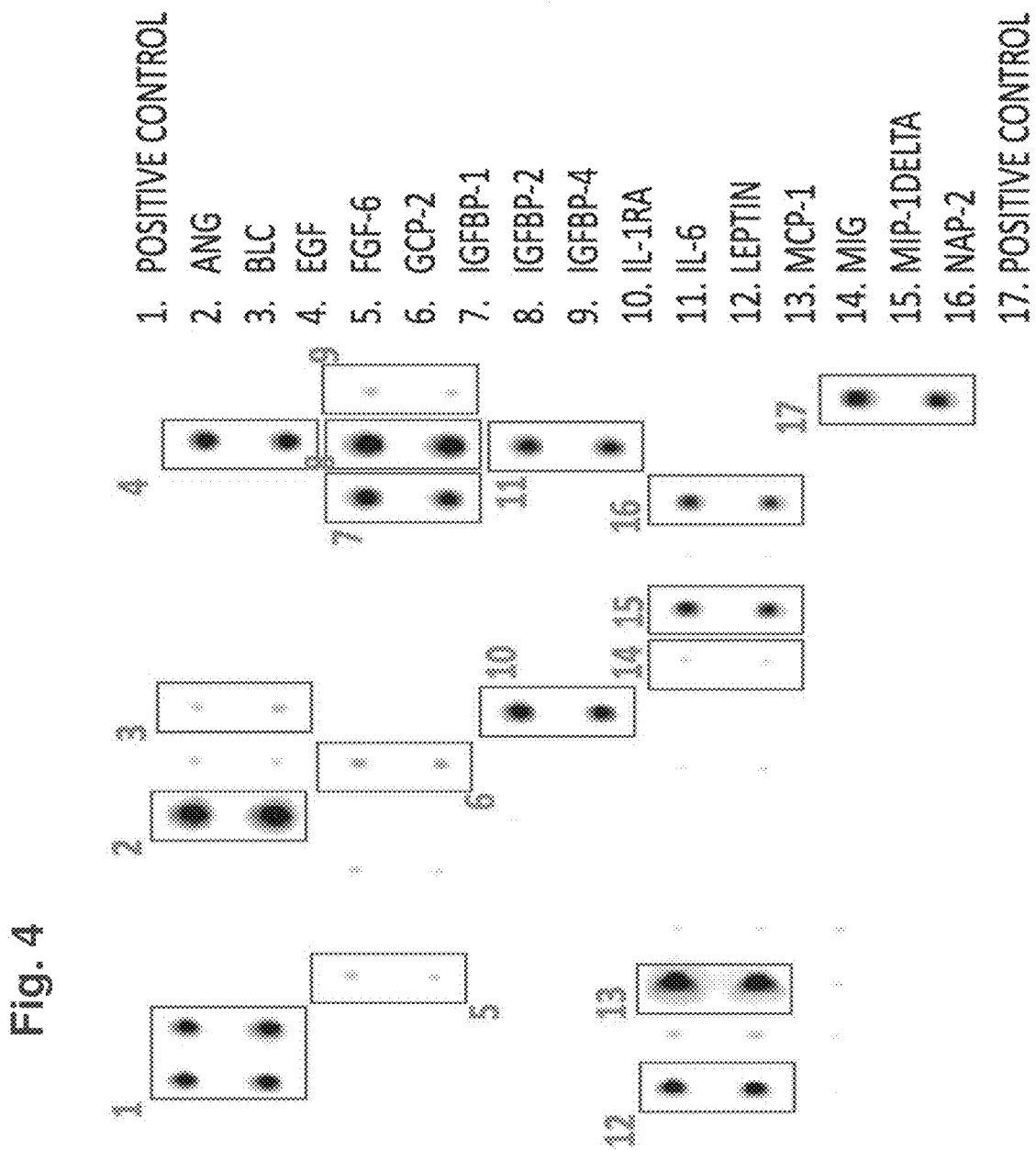
FIG. 4 shows a representative Dot Blot Analysis (Analysis #1) indicating the presence of, and relative concentrations of, selected cytokines and growth factors in a therapeutic composition described herein (e.g., Organicell Flow XL). The results for Organicell Flow provided similar results in this assay. Corresponding proteins are mapped and labelled, while relative expression level was determined by fold expression intensity to the average of the positive control spots.
Figure 5A:
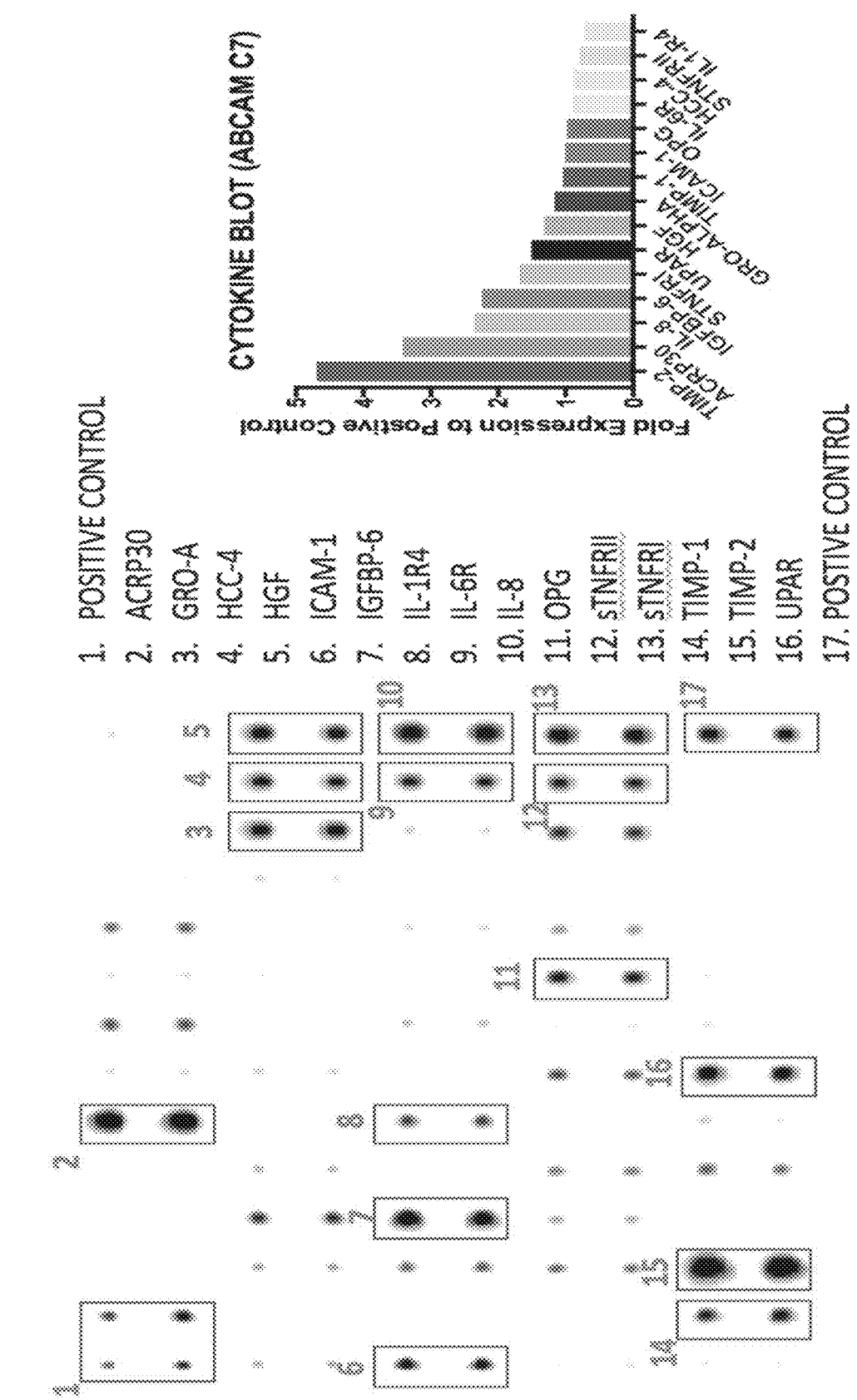
FIGS. 5A-5C show additional results of representative cytokine assays indicating the presence of, and relative concentrations of, selected cytokines and growth factors in a therapeutic composition described herein (e.g., Organicell Flow XL). The results for Organicell Flow XL and Organicell Flow provided similar results in these assays. Corresponding proteins are mapped and labelled, while relative expression level was determined by fold expression intensity to the average of the positive control spots.
Figure 5B:
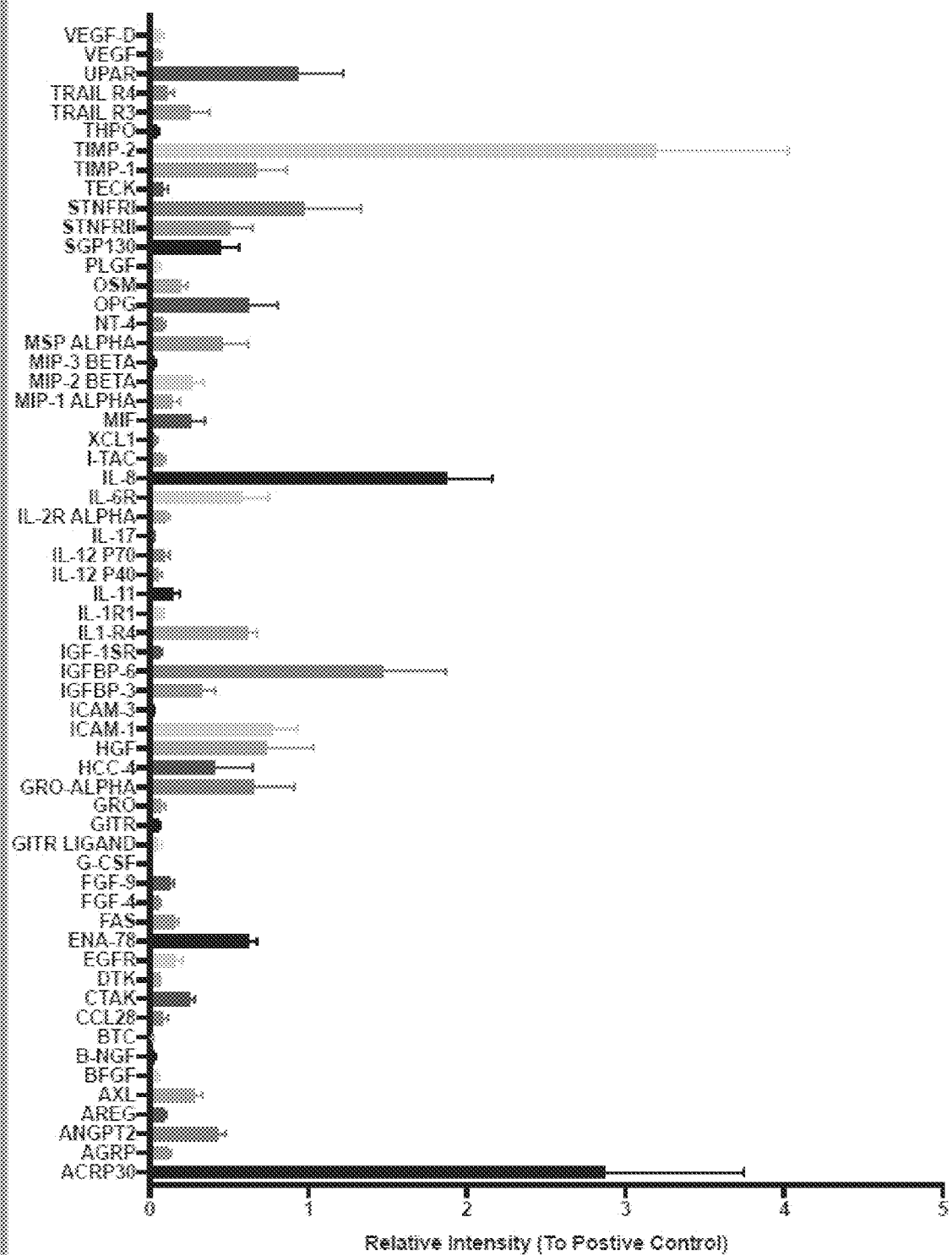
Figure 5C:
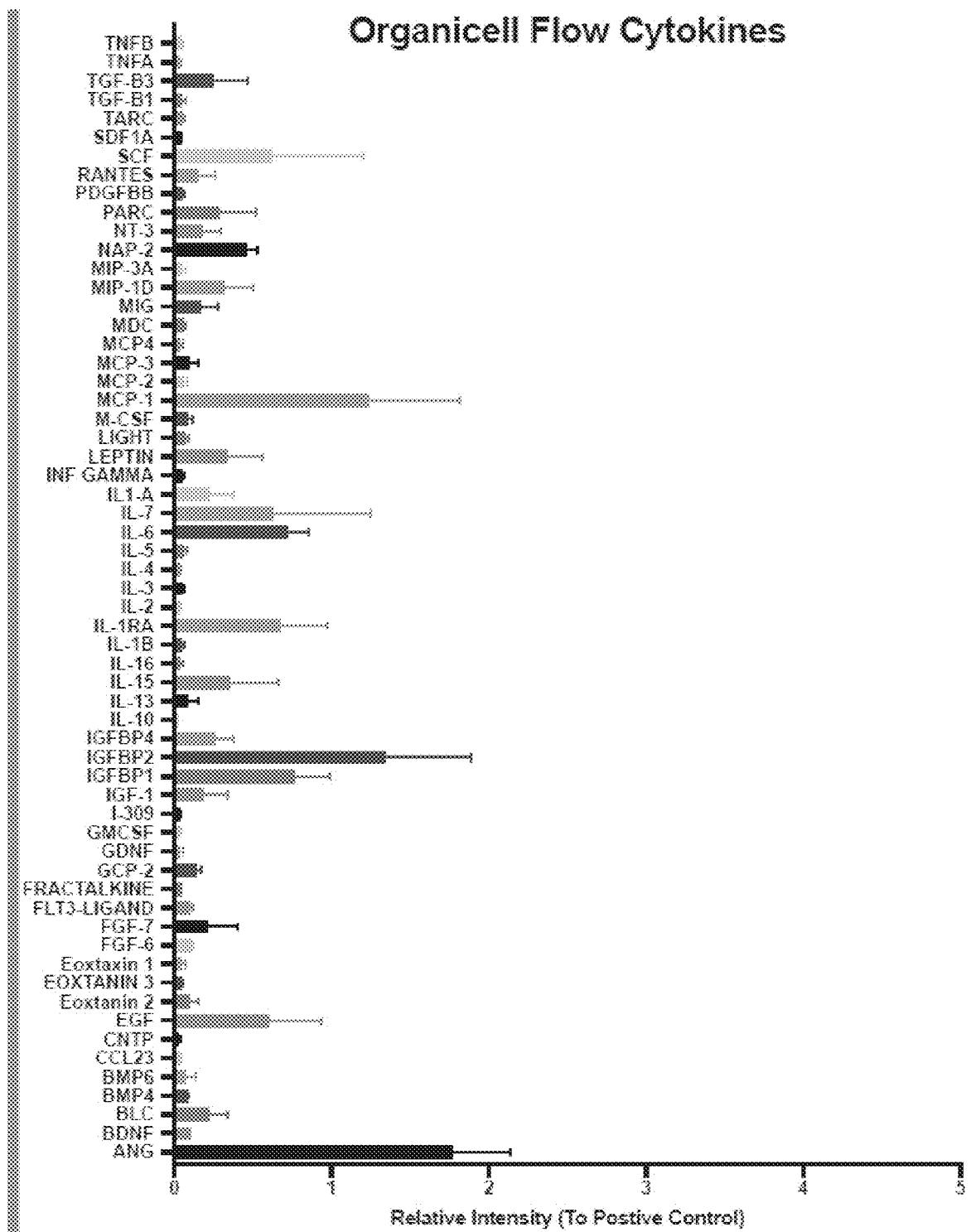
Figure 6:
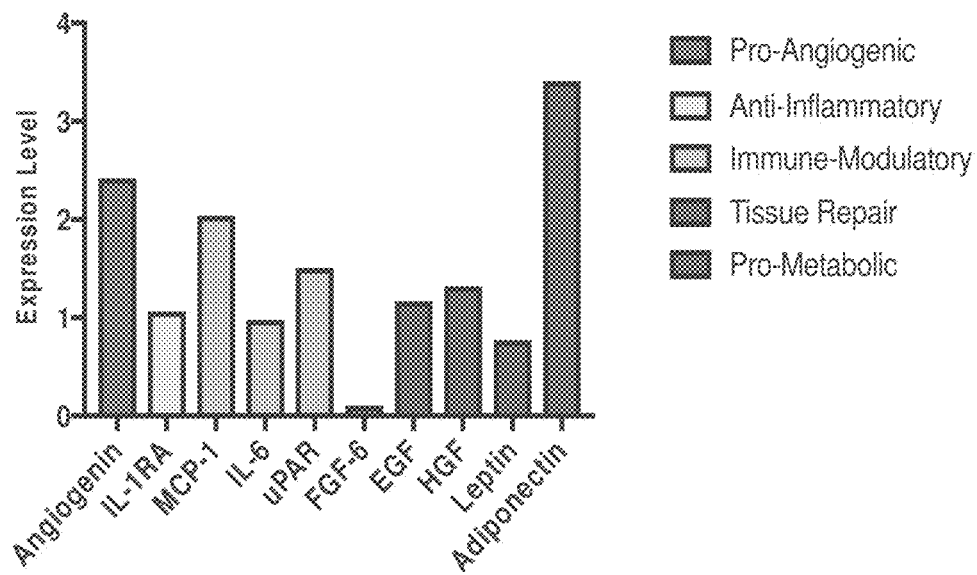
FIG. 6 shows a summary of the dot blot analysis of FIGS. 4 and 5 indicating the presence of, and relative concentrations of, selected cytokines and growth factors in a therapeutic composition described herein (e.g., Organicell Flow XL). The results for Organicell Flow provided similar results in this assay. The relative expression was calculated by the fold expression intensity compared to the average of the positive control spots. The completed dot blot analysis revealed several cytokines that regulate various aspects of tissue regeneration and repair (see color legend).
Figure 7:
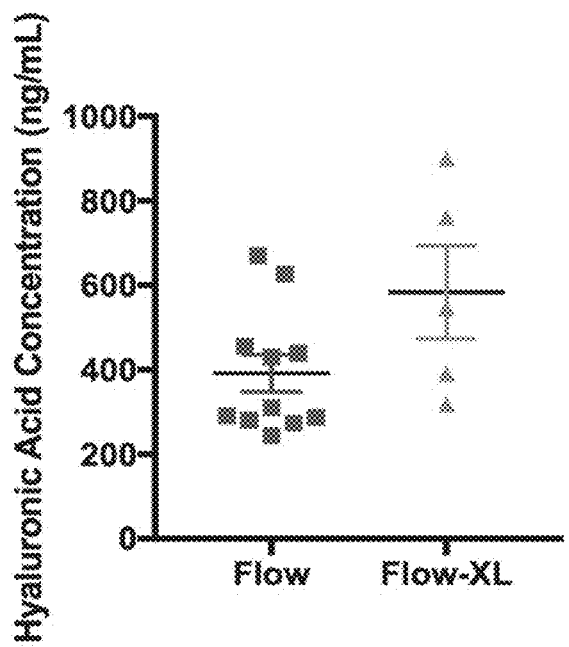
FIG. 7 shows the concentration of hyaluronic acid in Organicell Flow (Flow) & Organicell Flow XL (Flow XL) products.

The soluble protein compartment of Organicell Flow & Flow XL consisted of several cytokines, chemokines, growth factors and hyaluronic acid. Routine testing of the total soluble protein concentration in each Organicell Flow lot was conducted using Bradford protein analysis to ensure a reproducible protein concentration above about 1 mg/ml (FIG. 3). Several cytokine assays were also conducted to detect and semi-quantitatively measure the amount of cytokines and growth factors present in the Flow and Flow XL products (FIGS. 4, 5A-5C & 6). The results showed that the Flow and Flow XL products contained a similar variety of pro-angiogenic, immune-modulatory[1], anti-inflammatory[2], pro-metabolism[3], and tissue repair growth factors[4] (FIGS. 4, 5 & 6). The Flow and Flow XL products also contained extracellular matrix components such as hyaluronic acid in a mean amount of about 400 ng/ml (Flow) to about 550 ng/ml (Flow XL) (FIG. 7).

Hyaluronic acid participates in a number of biological processes such as tissue healing, inflammation, water homeostasis, and inter-cell communication.

Figure 8C:
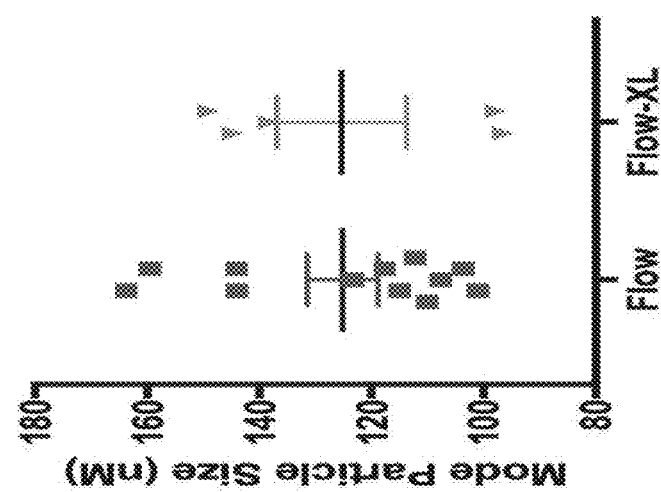
FIGS. 8A-8C shows a representative analysis of nanoparticle distribution (FIG. 8A), nanoparticle concentration (FIG. 8B) and nanoparticle mode particle size (FIG. 8C) in Organicell Flow (Flow) & Organicell Flow XL (Flow XL) products. Number of products analyzed: Flow=12/Flow XL=5.
Figure 8B:
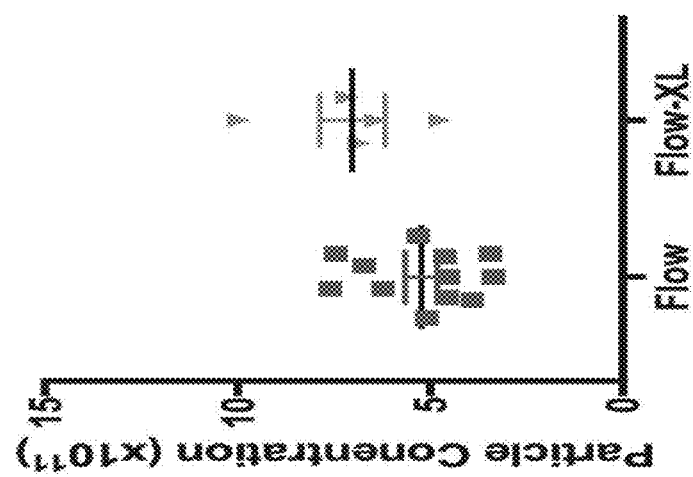
Figure 8A:
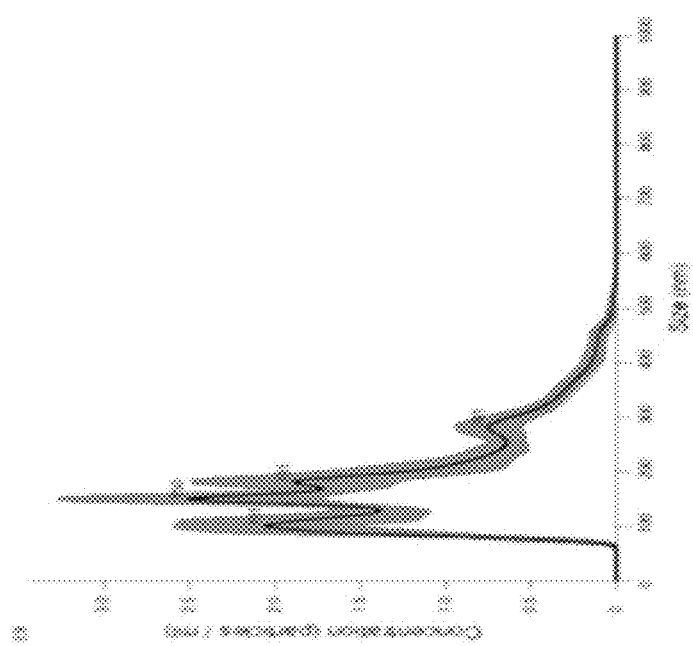

Nanoparticle analysis of the Flow and Flow XL products was conducted using the Nanosight NS300 (Malvern Panalytical) instrument. The results demonstrated a reproducible nanoparticle concentration in the final products with a mean concentration of $5.24 \times 10^{11}$ particles/ml and an average mode particle size of 125 nm (FIG. 8). The expected particle size of exosomes was 50-200 nm in diameter.

A MACsplex exosome surface marker array analysis was conducted to demonstrate that the nanoparticles observed in the Nanosight analysis were exosomes. Exosome markers CD63, CD81, and CD9 were detected in addition to surface markers associated with various subsets of exosome populations (FIG. 9, FIG. 10). Results of this analysis confirmed the expression of CD63, CD81, and CD9. Interestingly, the exosomes were found to express high levels of CD133 and CD326, two markers of epithelial and epithelial progenitor cell populations[5,6].

Figure 11:
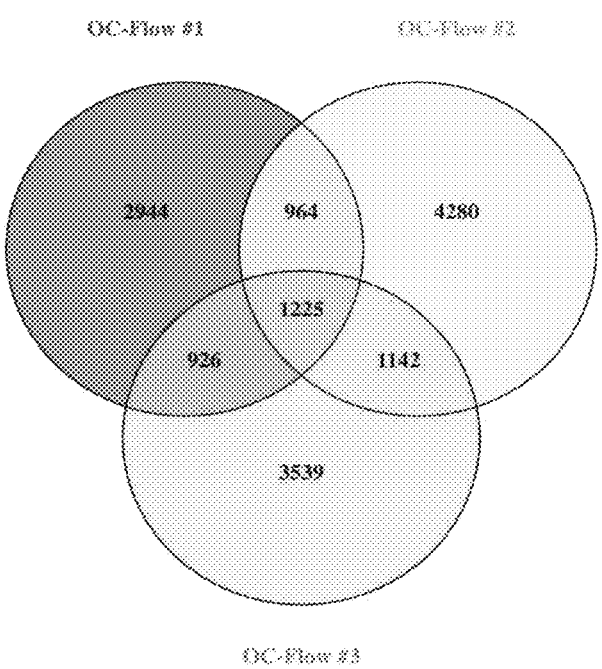
FIG. 11 shows a Vin diagram analysis of the 3 independent Organicell Flow compositions analyzed by mass spectrometry and the observed quantification of common and unique proteins.
Figure 12:
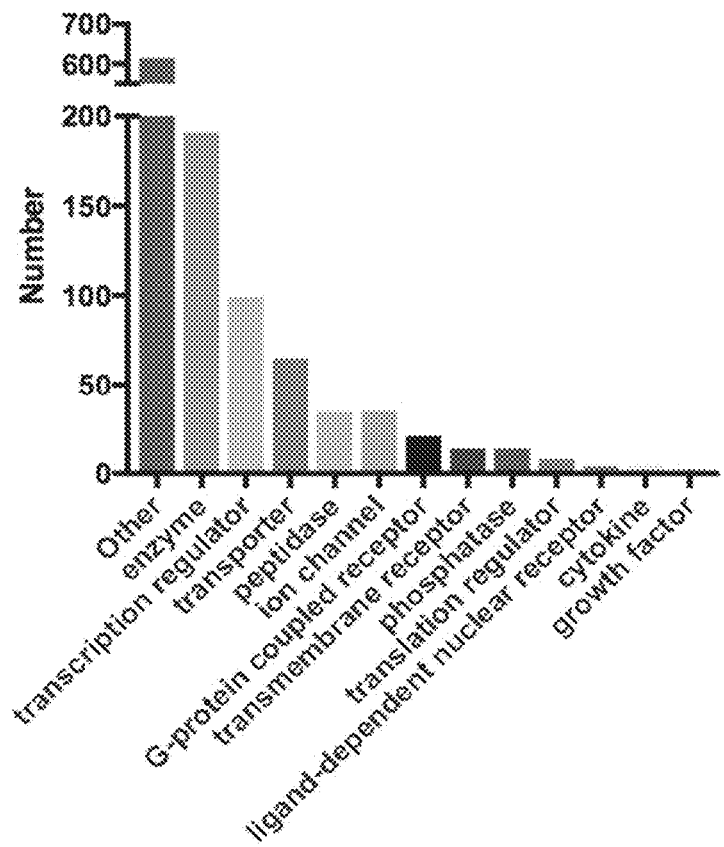
FIG. 12, shows 1225 common proteins detected in Organicell Flow categorized by protein type.
Figure 13:
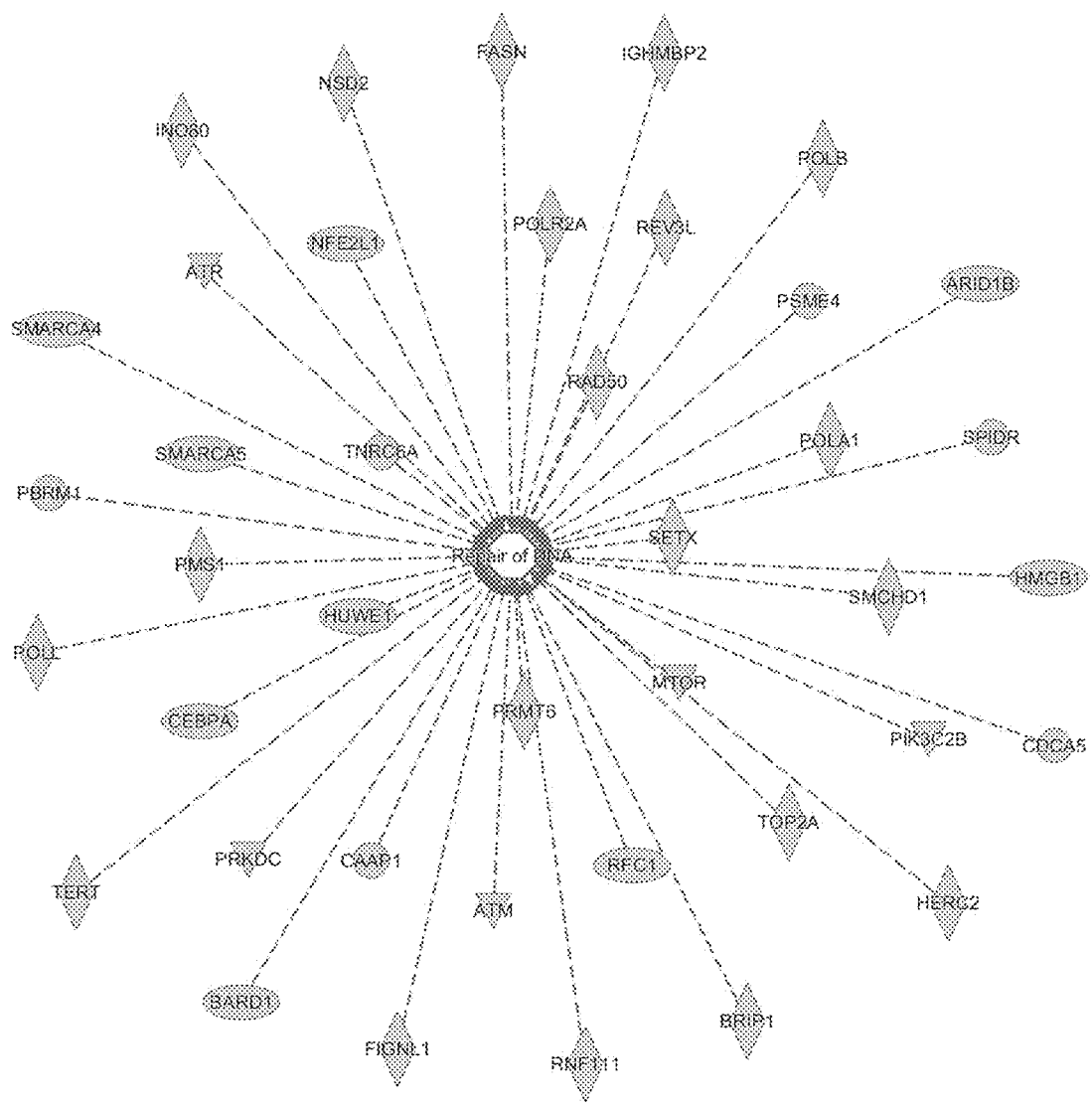
FIG. 13 shows a bioinformatics analysis of Organicell Flow protein cargo revealing 40 unique proteins involved in the regulation of DNA damage repair. Data analysis was completed using the Qiagen IPA software. Only those proteins known to have experimentally observed relationships are included within the analysis.

The lipid-bilayer nature of exosomes allows for efficient uptake of exosome cargo into the recipient cells. Two major components of exosome cargo that are well established mediators of exosome regeneration are protein and microRNA factors. To determine the protein cargo of exosomes, a mass spectrometry analysis was conducted using the Easy nLC 1000 and Q Exactive instruments. Exosomes were precipitated from Organicell Flow using size-exclusion filtration followed by ultracentrifugation from 3 independent products (in triplicate) and subjected to protein lysis. Tune (version 2.9) and Xcalibur (version 4.1) was used to collect data while Proteome Discoverer (version 2.2) was used to analyze data. Protein expression lists were created by merging the 3 sample replicates together and commonly expressed proteins were determined using Vinny 2.0 yin diagram analysis. WebGestalt tool kit classification system was used to identify top protein function and pathway hits. The completed analysis revealed 1225 commonly detected proteins across 3 products (FIG. 11). The top molecular functions of identified proteins included protein-binding, ion-binding, and nucleic acid-binding with enzymes, transcription regulators, and transporter proteins representing the most abundant protein groups (FIG. 12). Pathway enrichment analysis revealed top hits for Integrin, PDGF, and P53 pathways. A deeper dive into the enzyme category of the protein cargo further demonstrated the presence of proteins that promote DNA repair such as DNA polymerase (beta and lambda), telomerase reverse transcriptase, and RAD50 (FIG. 13).

Figure 14:
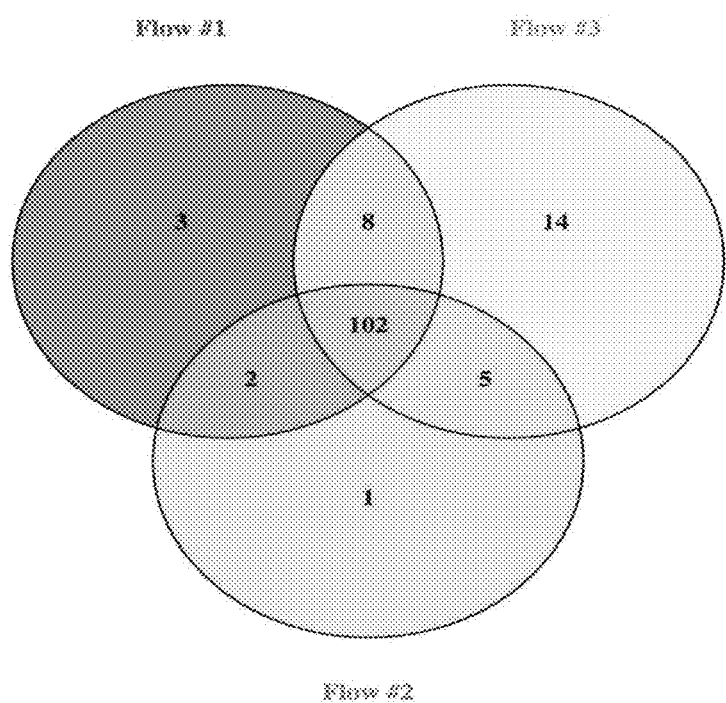
FIG. 14 shows 102 common mature miRNAs sequenced from Organicell Flow exosomes.
Figure 15:
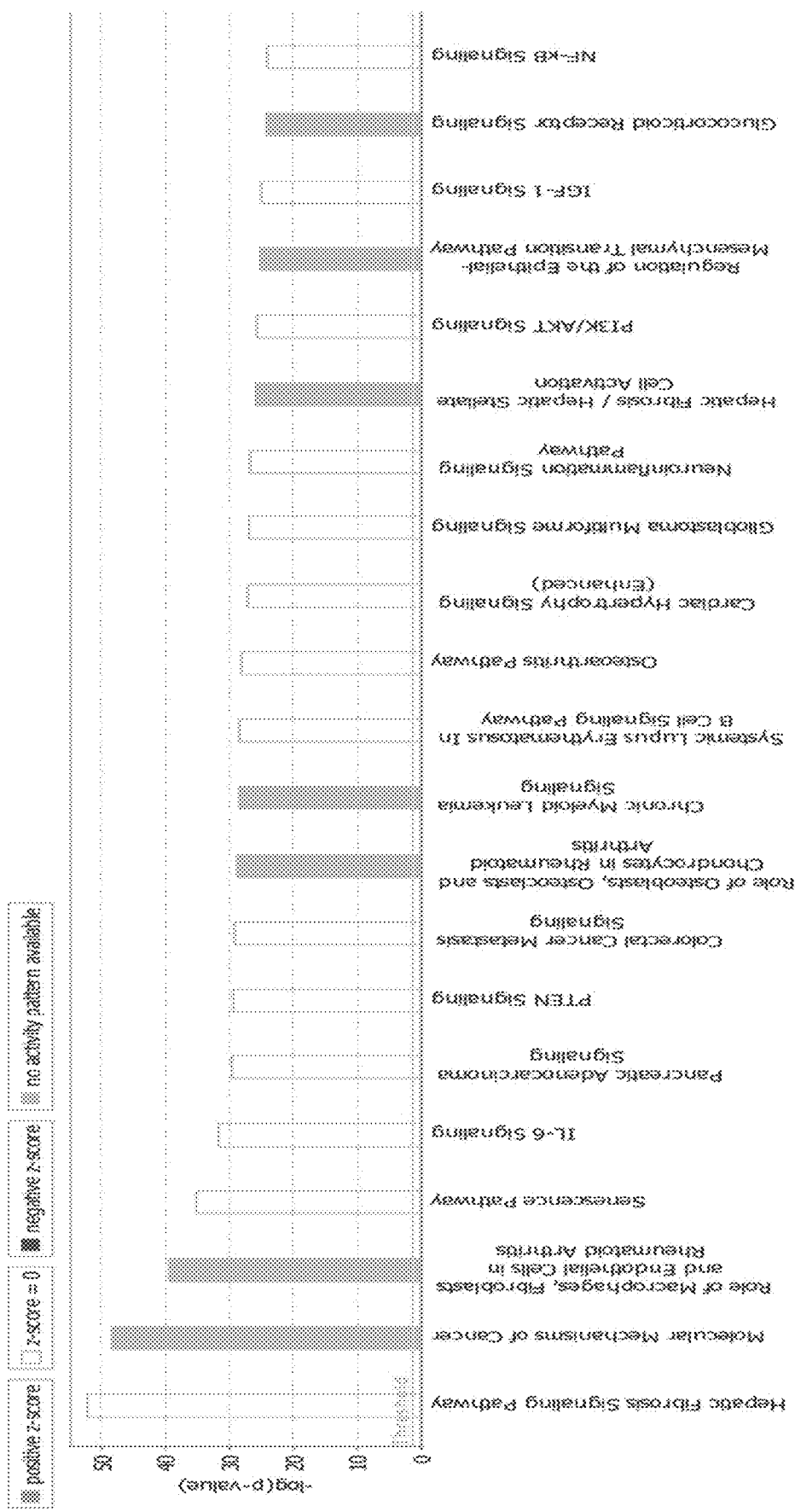
FIG. 15 shows a top canonical pathway analysis of the 1216 RNA targets of the identified Organicell Flow miRNA. This analysis reveals the top pathways most likely to be regulated by the delivery of miRNA cargo.

Exosomes were precipitated from 3 independent products (in triplicate) and subjected to RNA isolation for miRNA sequencing and identification (Table 1). The completed sequencing revealed 102 commonly expressed miRNAs (with a 100-copy expression minimum) (FIG. 14). Bioinformatics analysis was completed using the Qiagen IPA software to link 63 miRNAs to 1216 RNA targets. A top canonical pathway analysis of these mRNA targets reveals the regulation of various pathways such as hepatic fibrosis, senescence, interlukin-6 signaling, arthritis, IGF-1 and NFκ-B signaling (FIG. 15). Although miRNA functions vary, miRNA are powerful tools for the suppression of unwanted gene expression.

Figure 17:
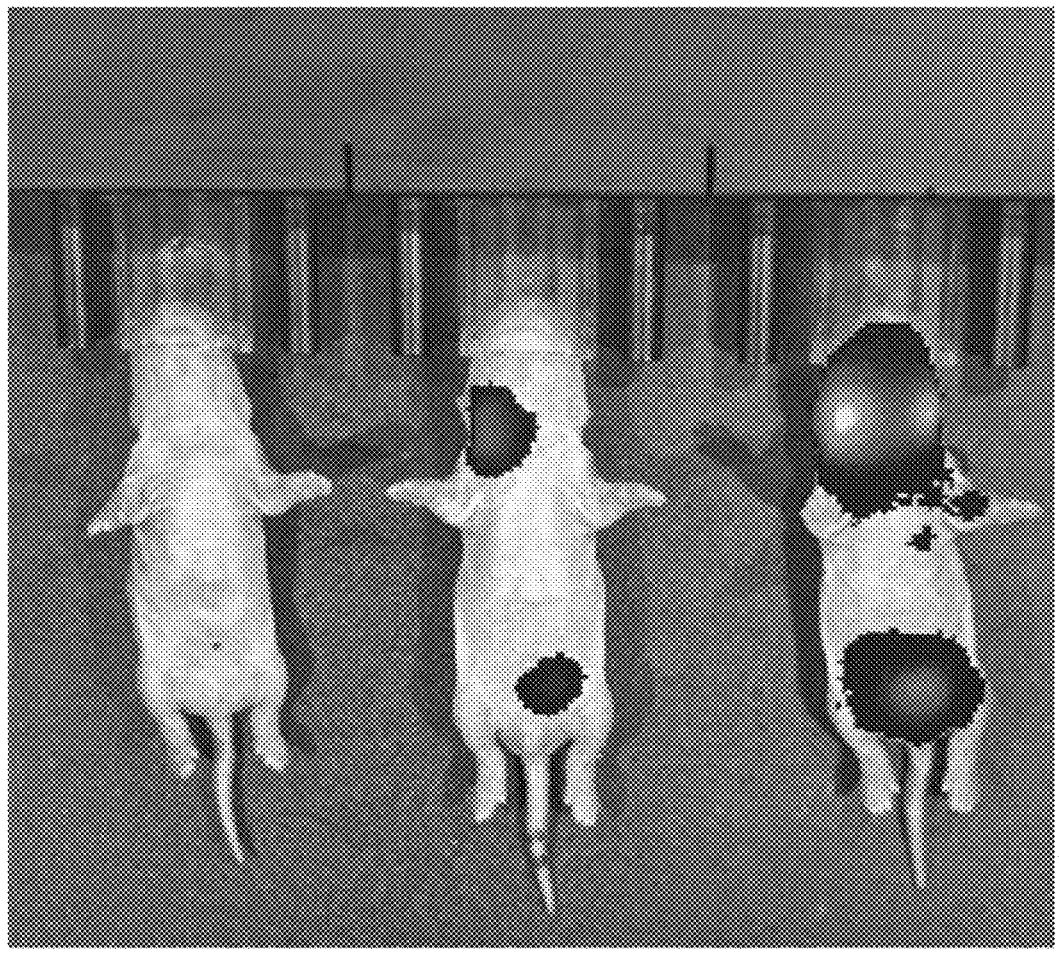
FIG. 17 shows IVIS live imaging of treated and control animals. Left: No dye control; Middle: Saline dye control; Right: Exosome dye treated.

A focused analysis of mRNA targets involved in COPD pathology revealed 25 miRNA that directly target 45 genes associated with COPD through experimentally observed relationships (FIG. 17). Of these 45 genes, several pro-inflammatory molecules stood out as potentially therapeutic targets for Organicell Flow exosomes. As such, Hsa-mir-21 was identified to target CXCL8 (IL-8) and TNFα while Hsa-mir-191 was linked to IL-6. The upregulation of pro-inflammatory cytokines such as CXCL8, TNFα, and IL-6 were associated with the increased progression of COPD. Similarly, Hsa-mir-146a was linked to the regulation of IL-1 receptor 1, a pro-inflammatory signaling receptor mediating the inflammatory signaling of IL-1. Aside from the identification of common mediators of inflammation and tissue injury, the completed analysis also revealed a potential mechanism that targets a novel mediator of COPD. The analysis linked hsa-mir-30d expression (the $3^{rd}$ highest expressed miRNA in Flow nanoparticles) to the regulation of WNT5a. Increased WNT5a expression mediates impairment in mesenchymal-epithelial cross talk in COPD pathology. In a murine model of elastase-induced emphysema, it was demonstrated that inhibition of WNT-5A via IgG neutralizing antibodies induces alveolar cell function. In summary, the identification of several miRNA in Flow and Flow XL that target inflammatory and COPD associated genes has allowed us to formulate potentially therapeutic mechanisms against this disorder. Based on this data, it was hypothesized that hsa-mir-30d, hsa-mir-191, hsa-mir-21, and has mir-146a can work synergistically to suppress the expression of WNT5a, IL1-R1, IL-6, CXCL8, and TNFα to attenuate the pathogenesis of COPD.

TABLE 1

| miRNA Cargo Composition from Organicell Exosomes | | |
|---|---|---|
| miRNA ID | Unique miRNA SEED Sequence | Counts |
| hsa-let-7b | let-7a-5p (and other miRNAs w/seed GAGGUAG) | 163836.63 |
| hsa-mir-200c | miR-200b-3p (and other miRNAs w/seed AAUACUG) | 143396.289 |
| hsa-mir-30d | miR-30c-5p (and other miRNAs w/seed GUAAACA) | 63969.738 |
| hsa-mir-125a | miR-125b-5p (and other miRNAs w/seed CCCUGAG) | 50582.86967 |
| hsa-mir-483 | miR-483-3p (miRNAs w/seed CACUCCU) | 43235.14133 |
| hsa-mir-34c | miR-34a-5p (and other miRNAs w/seed GGCAGUG) | 22605.17733 |
| hsa-mir-200a | miR-141-3p (and other miRNAs w/seed AACACUG) | 21488.112 |
| hsa-mir-148a | miR-148a-3p (and other miRNAs w/seed CAGUGCA) | 19064.15833 |
| hsa-mir-191 | miR-191-5p (and other miRNAs w/seed AACGGAA) | 17824.9 |
| hsa-mir-21 | miR-21-5p (and other miRNAs w/seed AGCUUAU) | 13813.88967 |
| hsa-mir-146a | miR-146a-5p (and other miRNAs w/seed GAGAACU) | 13717.14667 |
| hsa-mir-26b | miR-26a-5p (and other miRNAs w/seed UCAAGUA) | 13485.69133 |
| hsa-mir-92b | miR-92a-3p (and other miRNAs w/seed ATJUGCAC) | 11927.01867 |
| hsa-mir-342 | miR-342-3p (miRNAs w/seed CUCACAC) | 11751.42133 |
| hsa-mir-34b | | 10938.98867 |
| hsa-mir-423 | miR-423-3p (miRNAs w/seed GCUCGGU) | 10817.33167 |
| hsa-mir-205 | miR-205-5p (and other miRNAs w/seed CCUUCAU) | 10032.47333 |
| hsa-mir-203a | miR-203a-3p (and other miRNAs w/seed UGAAAUG) | 9503.219333 |
| hsa-mir-99b | miR-100-5p (and other miRNAs w/seed ACCCGUA) | 9080.26733 |
| hsa-mir-375 | miR-375-3p (miRNAs w/seed UUGUUCG) | 7743.281667 |
| hsa-mir-10b | miR-10a-5p (and other miRNAs w/seed ACCCUGU) | 7641.076333 |
| hsa-mir-449c | miR-2682-5p (and other miRNAs w/seed AGGCAGU) | 7334.175333 |
| hsa-mir-320a | miR-320b (and other miRNAs w/seed AAAGCUG) | 7300.472 |
| hsa-let-7f-2 | | 7294.493667 |
| hsa-mir-23a | miR-23a-3p (and other miRNAs w/seed UCACAUU) | 5352.487667 |
| hsa-mir-27b | miR-27a-3p (and other miRNAs w/seed UCACAGU) | 5201.610333 |
| hsa-mir-93 | miR-17-5p (and other miRNAs w/seed AAAGUGC) | 5111.682333 |
| hsa-mir-221 | miR-221-3p (and other miRNAs w/seed GCUACAU) | 5018.618667 |
| hsa-mir-425 | | 4352.848 |
| hsa-mir-151a | | 4089.194 |
| hsa-mir-190b | miR-190a-5p (and other miRNAs w/seed GAUAUGU) | 3319.57 |
| hsa-mir-223 | miR-223-3p (miRNAs w/seed GUCAGUU) | 3258.624667 |
| hsa-mir-1180 | miR-1180-3p (miRNAs w/seed UUCCGGC) | 2796.347667 |
| hsa-mir-184 | miR-184 (and other miRNAs w/seed GGACGGA) | 2440.443667 |
| hsa-mir-361 | miR-361-5p (miRNAs w/seed UAUCAGA) | 2400.271333 |

TABLE 1-continued miRNA Cargo Composition from Organicell Exosomes

| miRNA ID | Unique miRNA SEED Sequence | Counts |
|---|---|---|
| hsa-mir-182 | miR-182-5p (and other miRNAs w/seed UUGGCAA) | 2129.35 |
| hsa-mir-92a-1 | | 1802.757667 |
| hsa-mir-29a | miR-29b-3p (and other miRNAs w/seed AGCACCA) | 1778.564333 |
| hsa-mir-183 | miR-183-5p (miRNAs w/seed AUGGCAC) | 1575.199 |
| hsa-mir-204 | miR-204-5p (and other miRNAs w/seed UCCCUUU) | 1527.485333 |
| hsa-mir-574 | miR-574-3p (miRNAs w/seed ACGCUCA) | 1462.388667 |
| hsa-mir-532 | miR-532-5p (and other miRNAs w/seed AUGCCUU) | 1358.51 |
| hsa-mir-28 | miR-708-5p (and other miRNAs w/seed AGGAGCU) | 1262.526667 |
| hsa-mir-744 | miR-744-5p (and other miRNAs w/seed GCGGGGC) | 1084.911 |
| hsa-mir-2110 | miR-2110 (and other miRNAs w/seed UGGGGAA) | 1054.646667 |
| hsa-mir-140 | miR-140-5p (and other miRNAs w/seed AGUGGUU) | 943.74 |
| hsa-mir-1307 | miR-1307-3p (miRNAs w/seed CUCGGCG) | 892.7326667 |
| hsa-mir-193b | miR-193a-3p (and other miRNAs w/seed ACUGGCC) | 849.2083333 |
| hsa-mir-660 | miR-660-5p (and other miRNAs w/seed ACCCAUU) | 792.8756667 |
| hsa-mir-224 | miR-125b-2-3p (and other miRNAs w/seed CAAGUCA) | 743.967 |
| hsa-mir-196b | miR-196a-5p (and other miRNAs w/seed AGGUAGU) | 722.4733333 |
| hsa-mir-339 | miR-339-5p (and other miRNAs w/seed CCCUGUC) | 702.7996667 |
| hsa-mir-186 | miR-186-5p (miRNAs w/seed AAAGAAU) | 698.1536667 |
| hsa-mir-3065 | | 694.2023333 |
| hsa-mir-378a | | 647.5746667 |
| hsa-mir-16-1 | | 645.9713333 |
| hsa-mir-338 | miR-338-3p (miRNAs w/seed CCAGCAU) | 604.9653333 |
| hsa-mir-126 | miR-126a-3p (and other miRNAs w/seed CGUACCG) | 589.614 |
| hsa-mir-95 | miR-95-3p (miRNAs w/seed UCAACGG) | 546.3883333 |
| hsa-mir-142 | | 538.7076667 |
| hsa-mir-328 | miR-328-3p (and other miRNAs w/seed UGGCCCU) | 533.523 |
| hsa-mir-335 | miR-335-5p (and other miRNAs w/seed CAAGAGC) | 520.7633333 |
| hsa-mir-125b-2 | | 520.584 |
| hsa-mir-149 | miR-149-5p (miRNAs w/seed CUGGCUC) | 513.9563333 |
| hsa-mir-150 | miR-150-5p (and other miRNAs w/seed CUCCCAA) | 512.378 |
| hsa-mir-181a-2 | | 481.0983333 |
| hsa-mir-769 | | 463.4003333 |
| hsa-mir-454 | miR-130a-3p (and other miRNAs w/seed AGUGCAA) | 445.0126667 |
| hsa-mir-625 | miR-625-5p (and other miRNAs w/seed GGGGGAA) | 437.8703333 |
| hsa-mir-664a | | 419.197 |
| hsa-mir-196a-2 | | 412.7143333 |
| hsa-mir-432 | miR-432 (and other miRNAs w/seed CUUGGAG) | 389.0573333 |

TABLE 1-continued miRNA Cargo Composition from Organicell Exosomes

| miRNA ID | Unique miRNA SEED Sequence | Counts |
| --- | --- | --- |
| hsa-mir-192 | miR-192-5p (and other miRNAs w/seed UGACCUA) | 383.2276667 |
| hsa-mir-127 | miR-127-3p (miRNAs w/seed CGGAUCC) | 378.358 |
| hsa-mir-382 | miR-382-5p (miRNAs w/seed AAGUUGU) | 350.487 |
| hsa-mir-642a | miR-642a-5p (miRNAs w/seed UCCCUCU) | 348.909 |
| hsa-mir-15b | miR-16-5p (and other miRNAs w/seed AGCAGCA) | 335.935 |
| hsa-mir-197 | miR-197-3p (and other miRNAs w/seed UCACCAC) | 332.446 |
| hsa-mir-185 | miR-185-5p (and other miRNAs w/seed GGAGAGA) | 319.874 |
| hsa-mir-135b | miR-135a-5p (and other miRNAs w/seed AUGGCUU) | 287.2496667 |
| hsa-mir-22 | miR-22-3p (miRNAs w/seed AGCUGCC) | 270.7673333 |
| hsa-mir-30c-2 | | 267.422 |
| hsa-mir-629 | | 259.3153333 |
| hsa-mir-451a | miR-451a (and other miRNAs w/seed AACCGUU) | 253.6816667 |
| hsa-mir-484 | miR-344a-5p (and other miRNAs seed CAGGCUC) | 253.021 |
| hsa-mir-671 | miR-671-5p (miRNAs w/seed GGAAGCC) | 250.5533333 |
| hsa-mir-210 | miR-210-3p (miRNAs w/seed UGUGCGU) | 250.25 |
| hsa-mir-4510 | miR-3103-5p (and other miRNAs w/seed GAGGGAG) | 243.6983333 |
| hsa-mir-324 | | 234.035 |
| hsa-mir-652 | miR-652-3p (miRNAs w/seed AUGGCGC) | 226.5896667 |
| hsa-mir-455 | miR-455-5p (and other miRNAs w/seed AUGUGCC) | 216.722 |
| hsa-mir-155 | miR-155-5p (miRNAs w/seed UAAUGCU) | 213.3816667 |
| hsa-mir-500a | miR-500a-5p (miRNAs w/seed AAUCCUU) | 213.1276667 |
| hsa-mir-31 | miR-31-5p (and other miRNAs w/seed GGCAAGA) | 206.0306667 |
| hsa-mir-3615 | miR-3615 (miRNAs w/seed CUCUCGG) | 193.3536667 |
| hsa-mir-3675 | | 186.9733333 |
| hsa-mir-345 | miR-345-5p (miRNAs w/seed CUGACUC) | 180.636 |
| hsa-mir-206 | miR-1-3p (and other miRNAs w/seed GGAAUGU) | 166.3153333 |
| hsa-mir-374a | miR-374b-5p (and other miRNAs w/seed UAUAAUA) | 159.2533333 |
| hsa-mir-340 | | 158.573 |
| hsa-mir-409 | | 156.0193333 |
| hsa-mir-26a-2 | | 111.9633333 |

Tests for Safety

The follow set of tests were completed on each Organicell Flow lot to ensure product safety and reproducibility:

(1) Sterility and Endotoxin Testing

Safety assessment was completed by performing endotoxin and 14-day sterility testing for the detection of bacteria, fungus, and yeast contamination. Endotoxin tests were completed in accordance to USP<85> guidelines and sterility tests were performed by VRL Eurofins, a qualified CLIA certified laboratory, in accordance to USP<71> guidelines. One vial was selected for endotoxin testing and 10% of the total lot volume was randomly selected for 14-day sterility testing at the completion of the processing procedure. The vial sample size selected for 14-day testing was determined by the USP<71> guidelines for the minimum volume and containers required based on total lot production size. Furthermore, in-process samples (2 mL total volume) were collected for 14-day sterile analysis at the beginning of amniotic fluid handling (Raw product sample) and prior to filtration (pre-filtration sample). Our release criteria for safety assessment states that endotoxin levels must be below 5 EU/ml and all samples must be negative for sterility.

(2) Bradford Analysis

Product composition testing was completed on every product to ensure lot to lot reproducibility and stability.

Bradford analysis was completed on every product to demonstrate a similarity in overall protein concentration (>1 mg/ml).

(3) Nanosight Nano-Tracking Analysis (NTA)

NTA analysis was completed to demonstrate the mode particle size and concentration falls within our expected range (<200 nM mode size and >1×10$^{10}$ particles per ml).

| Parameter | Test Method (SOP No.) | Specification |
|---|---|---|
| Sterility and Endotoxin Testing | OC-GEN-018 | Sterility: Negative Endotoxin: <5 EU/mL |
| Bradford Analysis | OC-TOF-008 | Protein Concentration >1.0 mg/mL |
| NTA analysis | OC-TOF-002 | Particle Concentration >1 × 10$^{10}$/mL Particle Mode Size <200 nM |

All products must meet the standard quality requirements to be deemed acceptable for clinical use. In the event a product lot fails to pass the minimum release criteria for safety and composition, a production investigation is performed by the quality assurance associated and laboratory director to determine the root cause. If positive sterility is reported, additional backup samples are sent for immediate testing. While backup results are pending, a deviation must be recorded, and batch record documents will be reviewed.

Example 2—Bronchopulmonary Dysplasia (BPD)

Figure 16A:
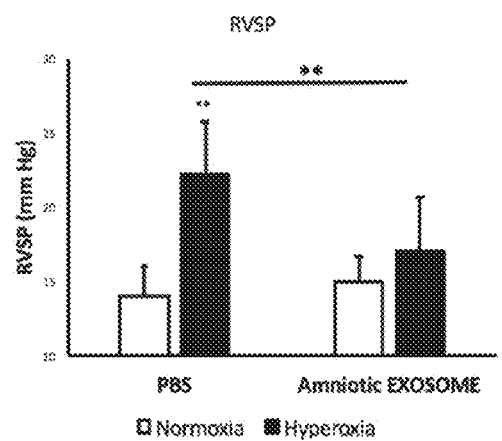
FIGS. 16A-16B shows an evaluation of Organicell Flow-XL in an established in vivo rat model of bronchopulmonary dysplasia (BPD).
Figure 16B:
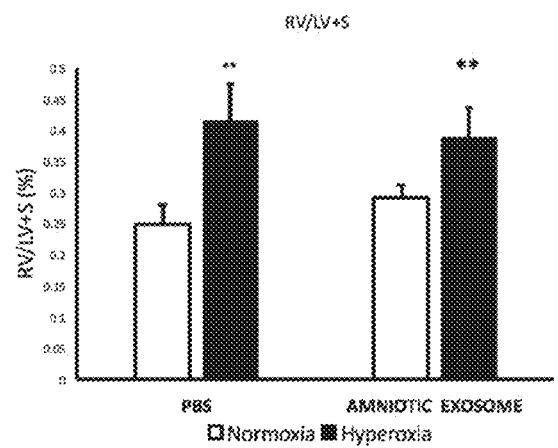

Studies were completed to test the safety and biological activity of the Organicell Flow-XL in a rat model of bronchopulmonary dysplasia (BPD)[8]. In this model, neonatal rat pups were placed in 85-90% oxygen for 3 days after birth to induce hyperoxic lung damage that is present in pre-mature infants diagnosed with BPD. After the 3 days in hyperoxia, Organicell Flow-XL or saline control was administered intratracheal and animals were allowed to recover for 14 days. Following the 14 day experiment, evaluation of survival and pulmonary hypertension (right ventricular systolic pressure and right ventricular hypertrophy) was completed. Survival assessment showed a 66% survival rate in saline treatment animals and a 100% survival rate in Flow-XL treated groups. Flow-XL decreased right ventricular systolic pressure compared to placebo (FIG. 16A) and provided a moderate (but not statistically significant) effect on right ventricular hypertrophy (FIG. 16B). Results of this study demonstrated a safety and biological activity of Flow-XL in an established animal model of lung disease. Successful retention of exosomes was confirmed by IVIS live imaging of infrared stained particles 2 hours after administration (FIG. 17).

Figure 24:
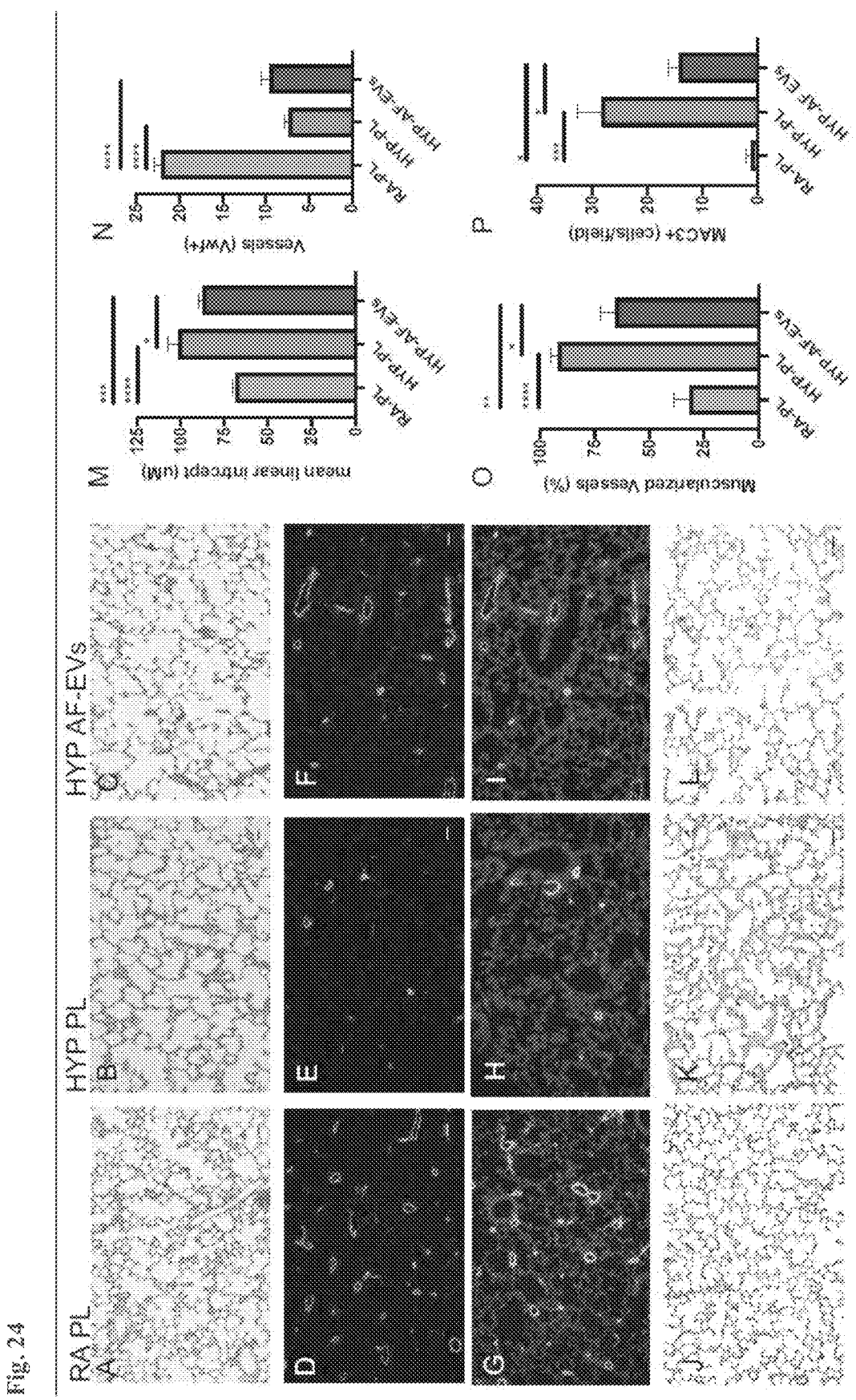
FIG. 24 shows effect of Organicell Flow-XL administration on Lung Structure and Macrophage Infiltration: (A-C) Representative lung sections showing improved alveolar structure in HYP animals which received Organicell Flow-XL. (D-F) Representative immunofluorescent staining showing decreased Von Willebrand Factor (vWF) immunostaining (green) in HYP groups. (G-I) Representative immunofluorescent staining of lung sections showing increased pulmonary vascular muscularization in HYP groups, Green=vWF, red=α-smooth muscle actin. (J-L) Representative lung sections immunostained with MAC-3 antibody (brown) showing decreased MAC-3 staining in HYP group, which received Organicell Flow-XL. (M) Reduced mean linear intercept in HYP group which received Organicell Flow-XL (n=4-7/group). (N) No significant difference in vascular density in the HYP groups (n=6/group). (O) Quantification of the average percentage of muscularized vessels revealed reduced vascular remodeling in the HYP group which received Organicell Flow-XL (n=5-6/group) (P) Quantification of the average number of MAC-3+ cells in all groups (n=4-5/group). Error bars represent standard error of the mean. *p-value<0.05, *p-value<0.001, **p-value<0.0001.

Histological analysis of the lung tissue revealed improved alveolar structure in the hyperoxia-exposed (HYP) group who received Flow-XL treatment. Alveolarization was determined by calculating the mean linear intercept (MLI). Morphometric analysis revealed a significant reduction in the MLI in the HYP group which received Flow-XL treatment (87.4±2.5 μm) compared to HYP-PL (101±6.1 μm, p-value<0.05) (FIGS. 24A-C, M). Vascular density also decreased in the placebo (PL) treated HYP (HYP-PL) group (7.33±0.6 vessels per HPF, p-value<0.0001) compared to PL-treated room air (RA) control (RA-PL) (22.2±0.8 vessel per HPF). Vascular density in the HYP group increased with Flow-XL treatment (9.5±1.0 vessels per HPF) (FIG. 24D-F, N).

Pulmonary vascular remodeling was assessed by quantifying the percentage of muscularized vessels. Animals in the HYP-PL group had significantly increased pulmonary vascular remodeling (92.0±3.3% muscularized pulmonary vessels, p-value<0.0001) compared to RA-PL (31.33±7.1% muscularized pulmonary vessels). Flow-XL treatment significantly reduced muscularization compared to HYP-PL (65.7±6.6% muscularized pulmonary vessels, p-value<0.05) (FIGS. 24G-I, O). Immune response to the hyperoxia injury was measured by macrophage infiltration into the lung tissue via Mac-3 immunostaining. Macrophage infiltration increased in response to hyperoxia in the HYP-PL group (28.2±4.4 Mac-3 positive cells/HPF, p-value<0.001) compared to RA-PL (0±1.0 Mac-3 positive cells/HPF). HYP animals that received Flow-XL, however had significantly reduced macrophage infiltration (14.20±4.4 Mac-3 positive cells/HPF, p-value<0.05) compared to HYP-PL (FIG. 24J-L, P).

Example 3—Inflammation

Figure 18:
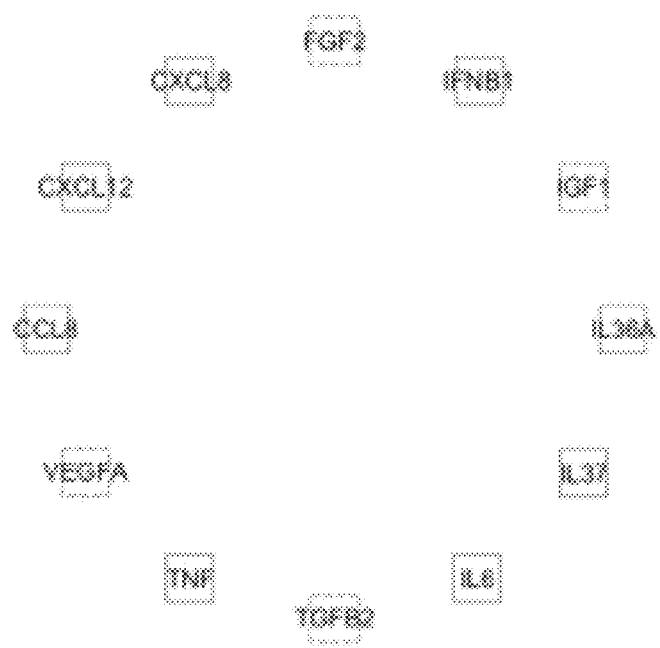
FIG. 18 shows Organicell miRNA targets involved in cytokine mediated immune responses.

Bioinformatics analysis linked 63 miRNAs to 1216 RNA targets. Major players involved in the pro-inflammatory cytokine and cytokine mediated immune response cascades found to be targeted by miRNA found in the Flow and Flow XL products include TNF, IL-6, and IL-8. Additionally, a broader array of pro-inflammatory cytokines also targeted by the collection of miRNA in the Flow and Flow XL products include FGF2, IFNB1, IGF1, IL36a, IL37, TGF-B2, VEGFA, CCL8, and CXCL12 (FIG. 18). Inhibition or suppression of this pro-inflammatory cytokine cascade may reduce the severity of symptoms associated elevated immune response[9]. Furthermore, miRNA in the exosome particles was found to target 148 genes associated with immune response. Together, this analysis suggests a therapeutic potential of the exosomes in immune-modulatory settings and as a potential therapy for the reduction of symptoms associated with lung inflammation (e.g., acute respiratory syndrome from COVID-19 infection).

Example 4—COVID-19 & Respiratory Distress Syndrome

Figure 19:
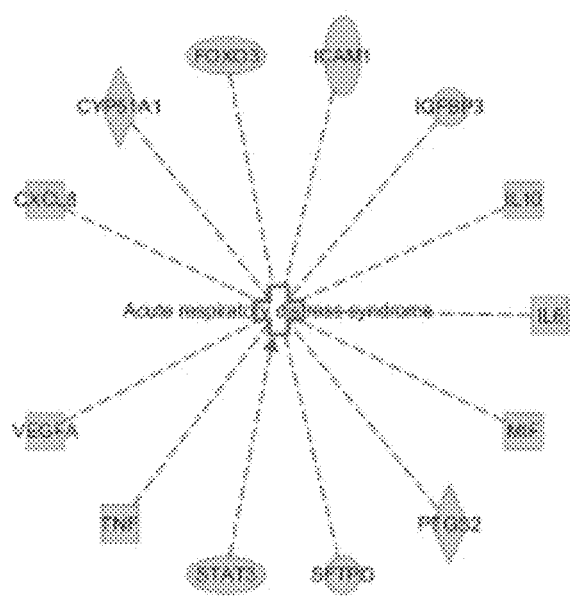
FIG. 19 shows Organicell miRNA gene targets associated with ARDS.
Figure 20:
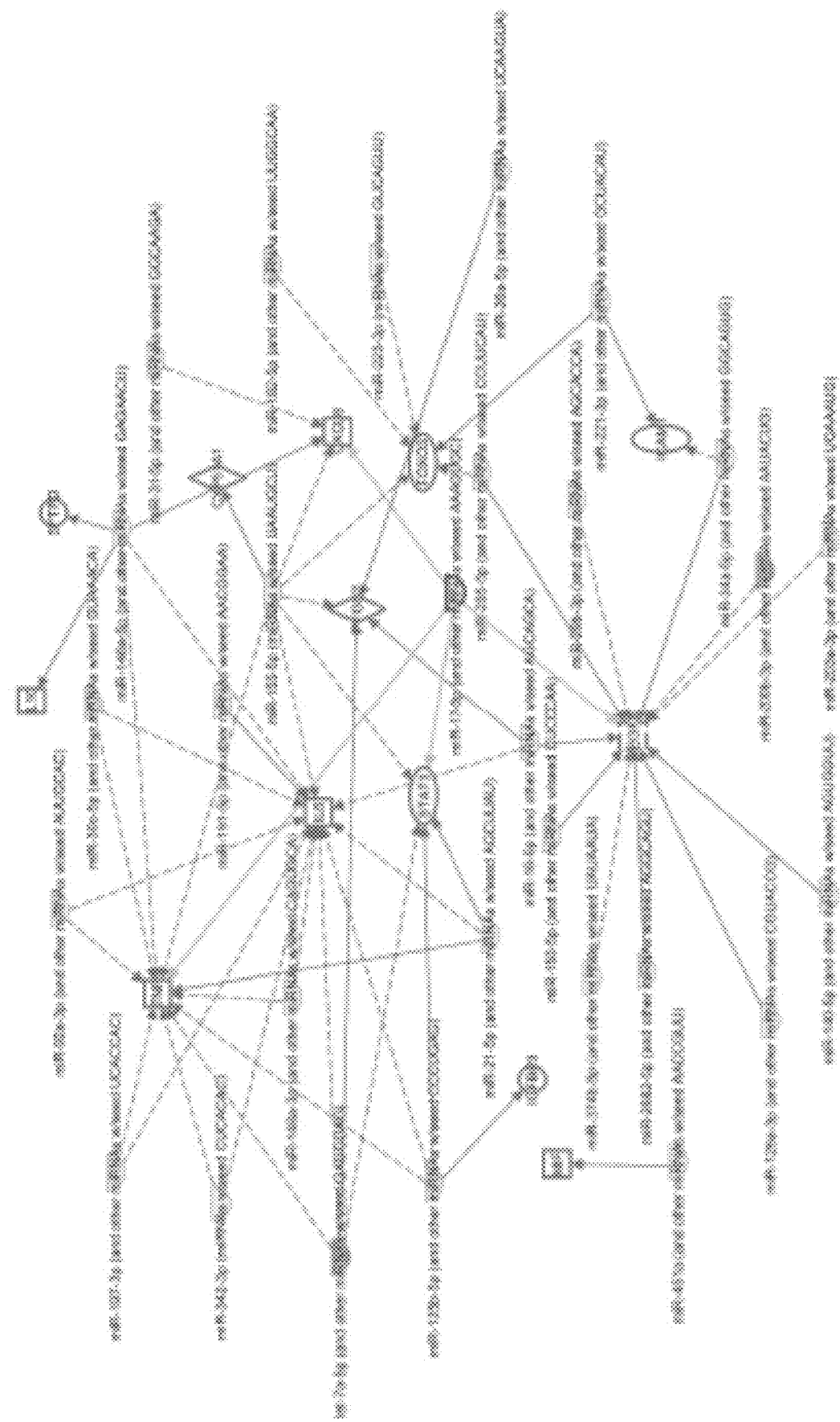
FIG. 20 shows Organicell's 60 different pathways identifying 29 miRNAs linked to ARDS genes.

One major complication of severe COVID-19 infection is the development of Acute Respiratory Distress Syndrome (ARDS). The risk of developing ARDS in a COVID-19 infection was linked to factors consistent with immune activation and a less robust immune response[9]. Extracellular vesicles derived from mesenchymal stem cells are expected to provide a significant role of protection against ARDS via the delivery of miRNA cargo such as miR-146a and miR-21-5-p found in Flow and Flow XL exosomes. Organicell Flow extracellular vesicles expressed both miR-146a and miR-21-5-p as well as 27 additionally identified miRNA that regulate 13 genes associated with ARDS disease. Representative ARDS gene targets include TNF, IL-6, FOXO3, IGFBP3, STATS, and COX-2 (FIGS. 18, 19 and 20). This bioinformatics analysis along with previously published results provides strong evidence that Organicell Flow may provide therapeutic relief in COVID-19 patients with ARDS and may be used as a novel treatment to reduce the overall severity of the infections. Together, this analysis suggests a therapeutic potential of Organicell extracellular vesicles in immune-modulatory settings and as a potential therapy for the reduction COVID-19 infection severity.

Example 5—Selected References

1. Hovius J W, Bijlsma M F, van der Windt G J, Wiersinga W J, Boukens B J, Coumou J, Oei A, de Beer R, de Vos A F, van't Veer C, van Dam A P, Wang P, Fikrig E, Levi M M, Roelofs J J and van der Poll T. The urokinase receptor (uPAR) facilitates clearance of Borrelia burgdorferi. *PLoS Pathog.* 2009; 5:e1000447.
2. Arend W P. The balance between IL-1 and IL-1Ra in disease. *Cytokine Growth Factor Rev.* 2002; 13:323-40.
3. Achari A E and Jain S K. Adiponectin, a Therapeutic Target for Obesity, Diabetes, and Endothelial Dysfunction. *Int J Mol Sci.* 2017; 18.
4. Johns D E and Athanasiou K A. Growth factor effects on costal chondrocytes for tissue engineering fibrocartilage. *Cell Tissue Res.* 2008; 333:439-47.
5. Koike C, Zhou K, Takeda Y, Fathy M, Okabe M, Yoshida T, Nakamura Y, Kato Y and Nikaido T. Characterization of amniotic stem cells. *Cell Reprogram.* 2014; 16:298-305.
6. Murphy S V, Kidyoor A, Reid T, Atala A, Wallace E M and Lim R. Isolation, cryopreservation and culture of human amnion epithelial cells for clinical applications. *J Vis Exp.* 2014.
8. Reiter J, Drummond S, Sammour I, Huang J, Florea V, Dornas P, Hare J M, Rodrigues C O and Young K C. Stromal derived factor-1 mediates the lung regenerative effects of mesenchymal stem cells in a rodent model of bronchopulmonary dysplasia. *Respir Res.* 2017; 18:137.
9. Liu Q, Zhou Y H and Yang Z Q. The cytokine storm of severe influenza and development of immunomodulatory therapy. Cell Mol Immunol. 2016; 13:3-10.
10. Wu C, Chen X, Cai Y, Xia J, Zhou X, Xu S, Huang H, Zhang L, Zhou X, Du C, Zhang Y, Song J, Wang S, Chao Y, Yang Z, Xu J, Zhou X, Chen D, Xiong W, Xu L, Zhou F, Jiang J, Bai C, Zheng J and Song Y. Risk Factors Associated With Acute Respiratory Distress Syndrome and Death in Patients With Coronavirus Disease 2019 Pneumonia in Wuhan, China. *JAMA Intern Med.* 2020.

Example 6—Osteoarthritis

This study enrolled five subjects: adults between the ages of 21 to 80 who have symptomatic osteoarthritis of the knee and who meet all inclusion/exclusion criteria. The study duration was one year. Subjects received 1 ml of Organicell Flow via IV infusion on day 0 and were followed up on day 0, week 1, and months 1, 3, 6, 9, and 12. No adverse events were observed post 3 months of the IV infusions. All subjects were closely monitored to observe product related adverse events for first 3 months. Subjects were continued to be monitored at 6, 9 and 12 months. The following demographics, baseline characteristics of knee OA and outcomes assessedare shown in Table 2 (subjects; n=5).

TABLE 2

Participant demographics and baseline characteristics.

| Parameter | OA Subjects |
|---|---|
| Age (years) | 61.0 ± 11.8 |
| Gender (Female/Male) | 1/3 |
| BMI (kg/m$^2$) | 36.34 ± 8.9 |
| Side of knee (n/%) | |
| Left | 3/75% |
| Right | 1/25% |
| WOMAC Score: | |
| Pain | 7.5 ± 5.4 |
| Stiffness | 5.3 ± 5.0 |

TABLE 2-continued

Participant demographics and baseline characteristics.

| Parameter | OA Subjects |
|---|---|
| Physical function | 43.0 ± 8.5 |
| Total | 59.5 ± 5.7 |

Safety of Organicell Flow Treatment

No adverse events were reported up to 4 hours post IV infusion, at 24 and 48 hours post IV infusions and at 1 months post IV infusions.

Efficacy

Figure 21:
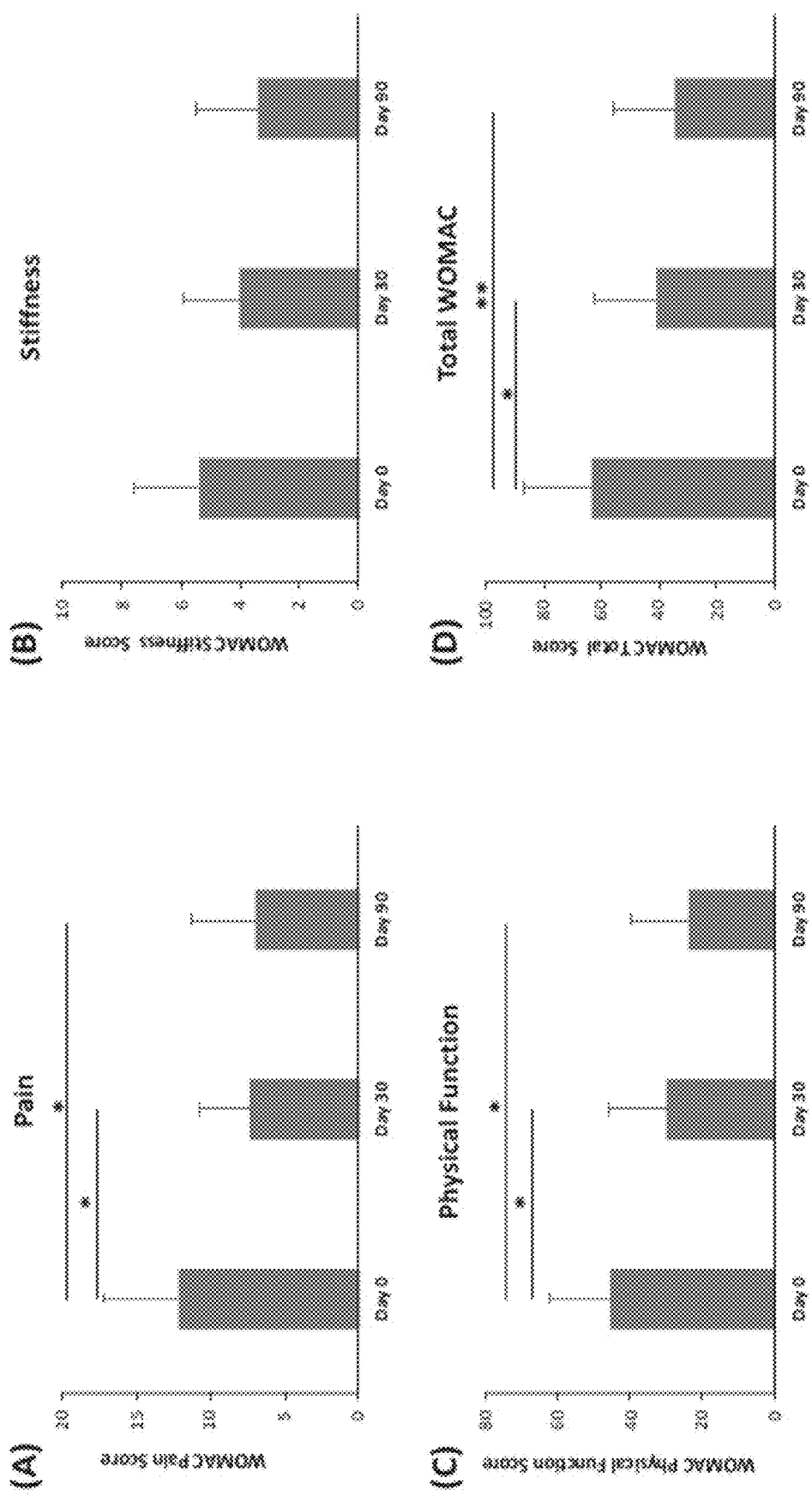
FIG. 21 shows Western Ontario and McMaster Universities Osteoarthritis Index (WOMAC) subscale scores at days 0, 30, and 90 for Pain (Panel A), Stiffness (Panel B), Physical function (Panel C) and Total WOMAC (Panel D). Data are represented as Mean±SD (n=5). Comparison of specific WOMAC subscale score among different time points was carried out by One-way ANOVA, p=0.01 (A), p=0.07 (B), p=0.003 (C), p=0.003 (D). Tukey's post-hoc test was used to compare difference in specific WOMAC score between each time points, *p<0.05, **p<0.01.
Figure 22:
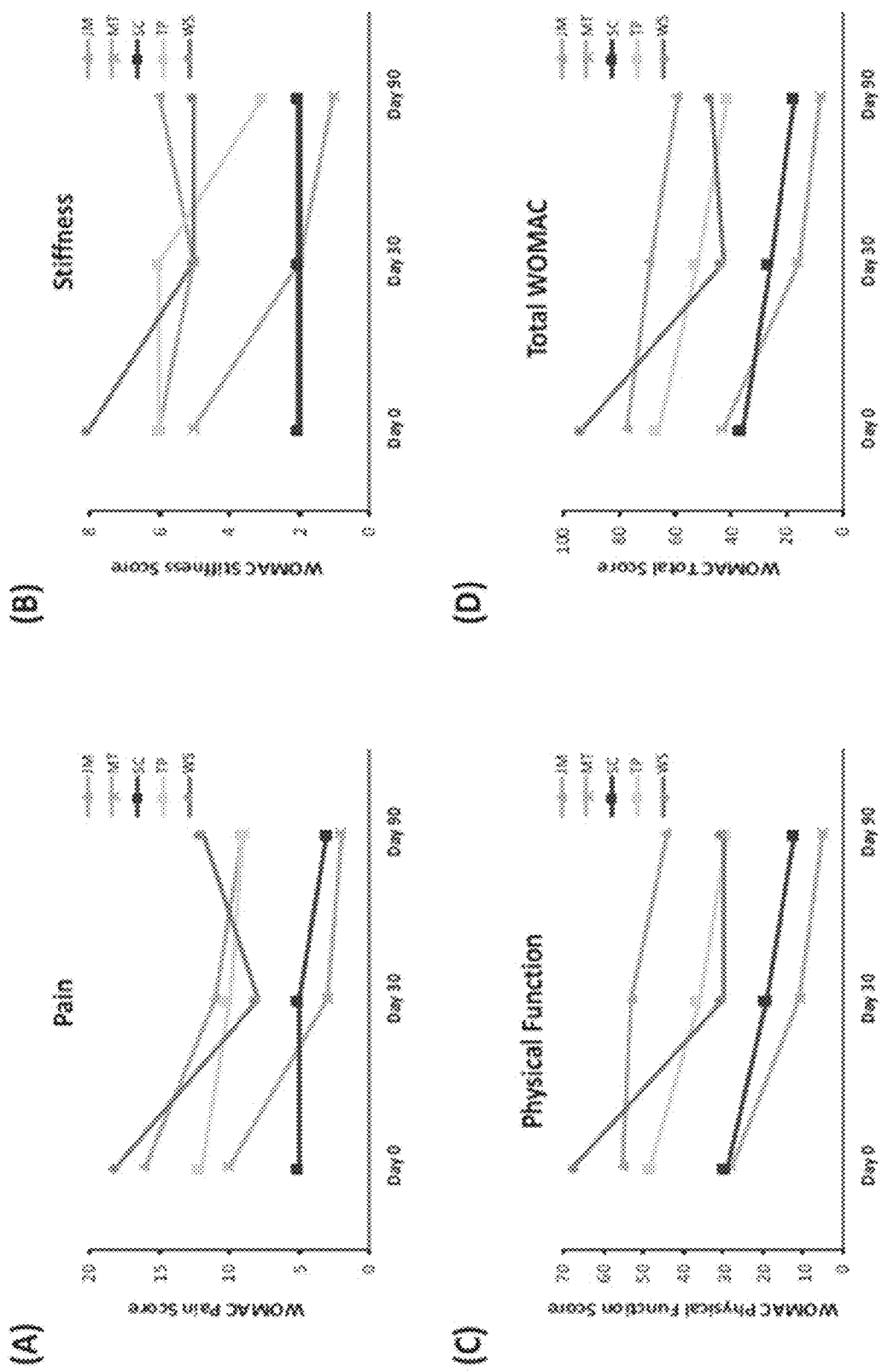
FIG. 22 shows WOMAC subscale scores for an individual patient at days 0, 30, and 90 for Pain (Panel A), Stiffness (Panel B), Physical function (Panel C) and Total WOMAC (Panel D). Each line represents specific WOMAC score of one patient at days 0, 30, and 90.
Figure 23A:
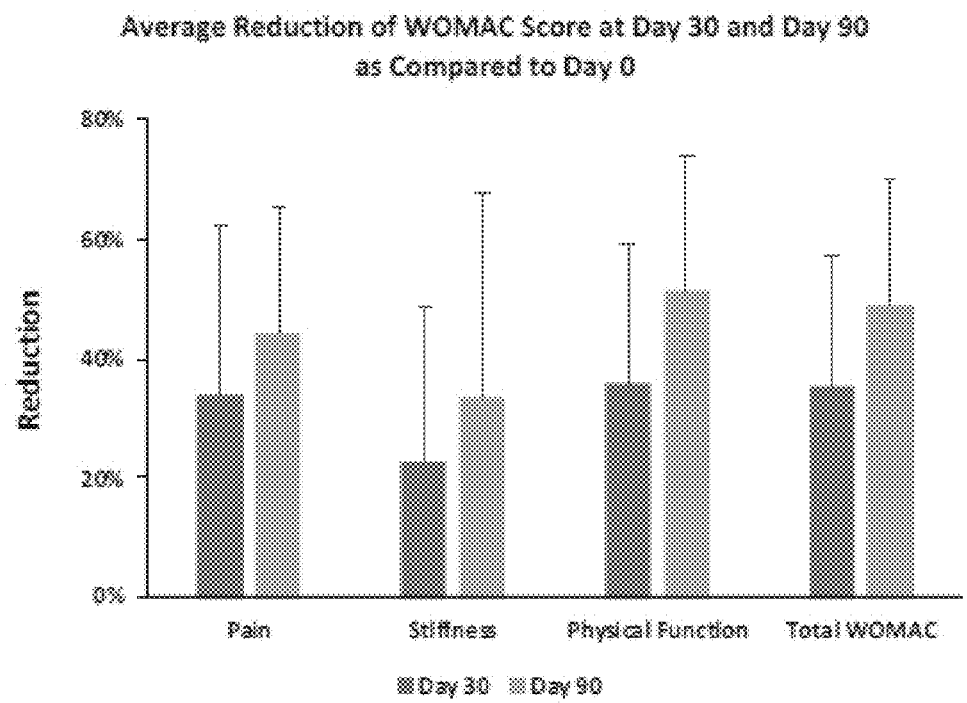
FIG. 23A shows the average reduction of WOMAC scores at day 30 and day 90 as compared to day 0.
Figure 23B:
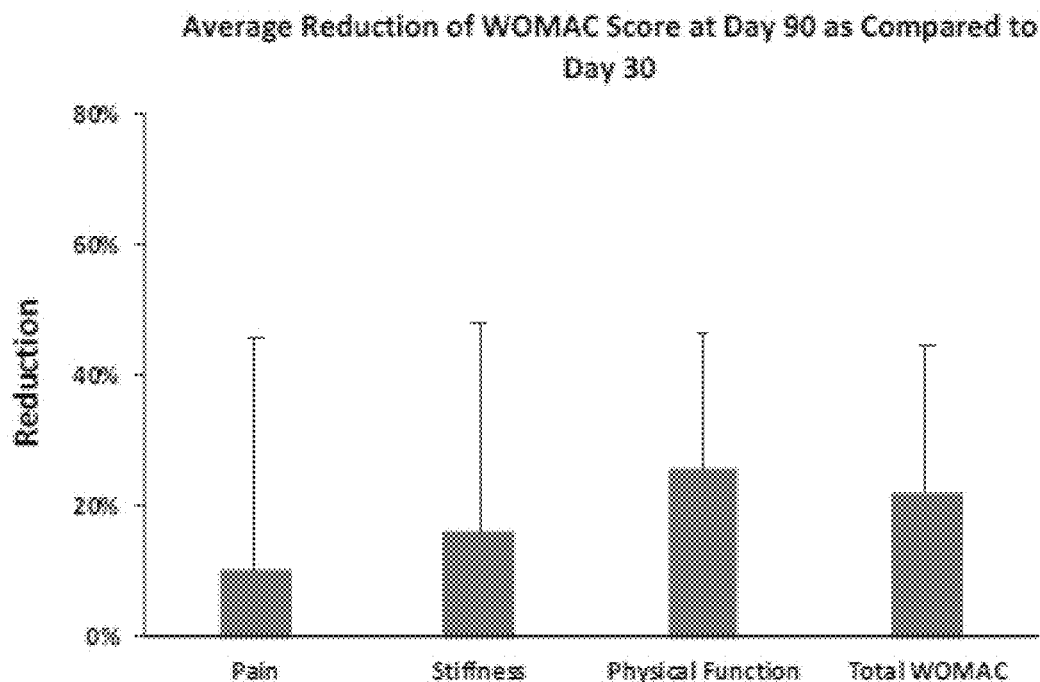
FIG. 23B shows the average reduction of WOMAC score at day 90 as compared to day 30. Data are represented as Mean reduction %±SD (n=5).

The effect of Organicell Flow treatment on WOMAC pain scores was assessed (FIG. 21A, FIG. 22A, FIG. 23, and Table 3A). The pain score of one patient did not have any change at day 30 as compared to day 0. For the rest of the four patients, pain score reduction ranged from 16.7%-70% at day 30 as compared to day 0. The pain score was decreased in all five patients at day 90 as compared to day 0, ranging from a 25% to 80% reduction in pain. Four out of five patients had further score reduction at day 90 as compared to day 30, ranging from 10%-40%; however, one patient had a 50% increase in the pain score on day 90 (score=12) as compared to day 30 (score=8).

The effect of Organicell Flow treatment on WOMAC stiffness scores was assessed (FIG. 21B, FIG. 22B, FIG. 23, and Table 3B). The average stiffness scores on day 0, day 30, and day 90 were 5.4±2.2, 4.0±1.9, and 3.4±2.1, respectively. At day 30, two patients had no stiffness score changes, and the other three had a score reduction ranged from 16.7% to 60% as compared to day 0. At day 90, two patients had no score changes, and the other three had a score reduction ranged from 37.5% to 80% as compared to day 0. As compared to day 30, two patients had no score changes, one patient had 20% increase (from 5 to 6), and the other two patients both had 50% reduction.

The effect of Organicell Flow treatment on WOMAC physical function scores was assessed (FIG. 21C, FIG. 22C, FIG. 23, and Table 3C). The physical function score is a measure of the restriction in the performance of an individual, such as difficulty getting up out of bed, getting up from a chair, walking, and climbing stairs. A high score indicates greater restriction of physical function. Accordingly, a decrease in the WOMAC physical function score indicated increased physical function. The WOMAC physical function score (mean±SD) was significantly reduced ($p<0.05$) on day 30 (29.8±16.2) and day 90 (24±15.5) as compared to the score at day 0 (45.4±16.9) indicating an improvement in physical function. Reduction in physical function ranged from 3.6% to 60.7% at day 30, and from 20% to 82.1% at day 90 as compared to day 0. Four out of the five patients had a further decrease in the score at day 90 as compared to day 30. The decrease ranged from 17% to 54.5%. The other patient had no change at day 30 and day 90. The effect of Organicell Flow treatment on WOMAC total score was assessed (FIG. 21D, FIG. 22D, FIG. 23, and Table 3D). The total WOMAC score was significantly improved at day 30 and day 90 as compared to day 0 ($p<0.05$). The average total score on day 0 was 63±23.6, while the scores at day 30 and day 90 were 41.2±21 and 34.4±21.3, respectively. The average reduction of the total WOMAC score at day 30 and day 90 was 35.2% (ranged 10.4%-62.8%) and 49% (ranged 23.4%-81.4%), respectively, compared to day 0. As compared to day 30, four out of the five patients had further reduction in total WOMAC score at day 90, ranging from 14.5% to 50%. The other patient had a 9.3% increase in the score at day 90 (from 43 to 47).

Overall, the data herein shows that Organicell Flow is effective at reducing pain and stiffness, and improving physical function in osteoarthritis.

TABLE 3A

Pain

| Pain | Initial | Day 0 | Day 30 | Day 90 | Reduction % Day 30 vs Day 0 | Reduction % Day 90 vs Day 0 | Reduction % Day 90 vs Day 30 |
|---|---|---|---|---|---|---|---|
| | JM | 16 | 11 | 9 | 31.3% | 43.8% | 18.2% |
| | MT | 10 | 3 | 2 | 70.0% | 80.0% | 33.3% |
| | SC | 5 | 5 | 3 | 0.0% | 40.0% | 40.0% |
| | TP | 12 | 10 | 9 | 16.7% | 25.0% | 10.0% |
| | WS | 18 | 8 | 12 | 55.6% | 33.3% | −50.0% |
| Average | | 12.2 | 7.4 | 7.0 | 33.8% | 44.4% | 10.3% |
| SD | | 5.1 | 3.4 | 4.3 | 28.4% | 21.1% | 35.7% |

TABLE 3B

Stiffness

| Stiffness | Initial | Day 0 | Day 30 | Day 90 | Reduction % Day 30 vs Day 0 | Reduction % Day 90 vs Day 0 | Reduction % Day 90 vs Day 30 |
|---|---|---|---|---|---|---|---|
| | JM | 6 | 5 | 6 | 16.7% | 0.0% | −20.0% |
| | MT | 5 | 2 | 1 | 60.0% | 80.0% | 50.0% |
| | SC | 2 | 2 | 2 | 0.0% | 0.0% | 0.0% |
| | TP | 6 | 6 | 3 | 0.0% | 50.0% | 50.0% |
| | WS | 8 | 5 | 5 | 37.5% | 37.5% | 0.0% |
| Average | | 5.4 | 4.0 | 3.4 | 22.8% | 33.5% | 16.0% |
| SD | | 2.2 | 1.9 | 2.1 | 25.9% | 34.3% | 32.1% |

TABLE 3C

Physical Function

| Physical Function | Initial | Day 0 | Day 30 | Day 90 | Reduction % Day 30 vs Day 0 | Reduction % Day 90 vs Day 0 | Reduction % Day 90 vs Day 30 |
|---|---|---|---|---|---|---|---|
| | JM | 55 | 53 | 44 | 3.6% | 20.0% | 17.0% |
| | MT | 28 | 11 | 5 | 60.7% | 82.1% | 54.5% |
| | SC | 29 | 19 | 12 | 34.5% | 58.6% | 36.8% |
| | TP | 48 | 36 | 29 | 25.0% | 39.6% | 19.4% |
| | WS | 67 | 30 | 30 | 55.2% | 55.2% | 0.0% |
| Average | | 45.4 | 29.8 | 24 | 35.8% | 51.1% | 25.6% |
| SD | | 16.9 | 16.2 | 15.5 | 23.2% | 23.1% | 20.8% |

TABLE 3D

Total WOMAC

| Total WOMAC | Initial | Day 0 | Day 30 | Day 90 | Reduction % Day 30 vs Day 0 | Reduction % Day 90 vs Day 0 | Reduction % Day 90 vs Day 30 |
|---|---|---|---|---|---|---|---|
| | JM | 77 | 69 | 59 | 10.4% | 23.4% | 14.5% |
| | MT | 43 | 16 | 8 | 62.8% | 81.4% | 50.0% |
| | SC | 36 | 26 | 17 | 27.8% | 52.8% | 34.6% |
| | TP | 66 | 52 | 41 | 21.2% | 37.9% | 21.2% |
| | WS | 93 | 43 | 47 | 53.8% | 49.5% | −9.3% |
| Average | | 63.0 | 41.2 | 34.4 | 35.2% | 49.0% | 22.2% |
| SD | | 23.6 | 21.0 | 21.3 | 22.2% | 21.5% | 22.2% |

Example 7—COVID-19, Acute Lung Injury, Acute Brain Injury, Acute Organ Failure

The primary objective of this study was to demonstrate safety, feasibility, and accessibility of Organicell Flow for the treatment of these severely ill Covid-19 patients, and to observe post-treatment changes in clinical status improvement and inflammatory biomarker improvement that may suggest potential therapeutic efficacy. Organicell Flow was prepared as described in Example 1. The specific parameters for the Organicell Flow administered in this study were: sterility (14-day cultures: no growth for aerobic, anaerobic, and fungal contamination), endotoxin (<0.05 EU/mL), nanoparticle composition (concentration=$3.26 \times 10^{11}$/mL, mode particle size=90.2 nm), protein concentration (2.83 mg/mL), and hyaluronic acid concentration (261 ng/mL).

Organicell Flow was administered to three critically ill Covid-19 patients concurrently with ongoing medical care who were monitored for 28-days post-therapy. All patients were diagnosed with COVID-19, developed respiratory failure, and were hospitalized for more than 40 days. All three patients suffered from severe, multi-organ complications induced by COVID-19 infection who were treated with Organicell Flow in addition to the authorized standard of care available at that time. These patients represent the subset of COVID-19 patients most effected by the virus. At the time of hospital admission there was no emergency authorized standard of care for COVID-19 infection. These patients were treated with supplemental oxygen, anti-inflammatories, antibiotics, antiviral medication, and other medications required to manage their multiorgan failure symptoms.

The first patient (de-identified subject CU #1) was a 74-year-old Caucasian female with multiple comorbidities including obesity, hypertension (HTN), type 2 diabetes, depression, hyperlipidemia (HLD), and vitamin D deficiency. This patient was initially admitted to the hospital 44 days prior to treatment at the study site. Initial diagnosis was acute hypoxemic respiratory failure with positive COVID-19 infection. The patient was orally intubated after 6 days in the hospital and treated for COVID-19 with pneumonia. COVID-19+ tests were reported for 20 days post-admission. Tracheostomy placement was performed prior to transfer to the study site. Patient CU #1 continued to require mechanical ventilation prior to treatment and developed acute metabolic encephalopathy with ICU delirium along with acute kidney injury and anemia. The initial COVID-19 treatment upon admission included a 10-day course of Hydroxychloroquine, three doses of Ribavarin, and Kaletra. Inclusion of additional medication was ongoing to manage complications induced by the multiple comorbidities. Ten days after transfer to the study site, Organicell Flow infusion was initiated in addition to ongoing medical treatment. Due to the patient's high BMI, it was decided to administer a total of four doses of Organicell Flow.

The second patient (de-identified subject CU #2) was a 79-year-old Caucasian female with multiple chronic comorbidities including obesity, HTN, HLD, Hodgkin's disease, hypothyroidism (HYT), and status post-left carotid endarterectomy. This patient was admitted to the hospital 47 days prior to treatment at the study site. Her initial diagnosis included septic syndrome and hypoxemic respiratory failure with positive COVID-19 infection. The initial treatment reports did not indicate if this patient received any anti-viral medication to target the COVID-19 infection; instead, the treatment included a wide range of medications to manage the severe symptoms associated with comorbidities, antibiotics (Cefepime and Vancomycin), and hemodialysis. Due to the severity of the patient upon admission, mechanical ventilation was immediately required after 2 days. The patient was extubated and then reintubated, followed by tracheostomy placement. COVID-19+ tests were reported for 16 days post-admission. Hospital course was complicated by acute kidney injury, anemia requiring blood transfusion, encephalopathy, and septic shock. The patient underwent PEG placement a few days prior to transfer to the study site. Transfer of the patient to the study site was completed for ventilator liberation and management of other comorbidities. The high BMI of CU #2 qualified this patient for four doses of Organicell Flow.

The third patient (de-identified subject CU #3) was a 66-year-old Hispanic male with comorbidities that included type 2 diabetes and HTN. This patient was admitted to the hospital 42 days prior to treatment at the study site. Initial diagnosis was hypoxemic respiratory failure secondary to COVID-19 pneumonia. Initial COVID-19 treatments included Hydroxychloroquine as an outpatient, followed by Tocilizumab on admission. Patient CU #3 required intubation that was followed by extubation and reintubation. Hospital course was complicated by hypoxemic cardiac arrest, acute kidney injury that required renal replacement therapy, acute DVT, and encephalopathy. The patient underwent tracheostomy prior to transfer to the study site. Transfer to the study site was completed for ventilator liberation, management of hemodialysis, continuation of nutritional support, and management of other comorbidities. COVID-19+ tests were reported for 8 days post-admission. Additional medication and antibiotics were incorporated throughout treatment as the patient's condition evolved. The patient received three doses of Organicell Flow beginning 9 days after transfer to the study site.

Methods

Sequential Organ Failure Assessment (SOFA) score assessment, chest X-rays, and inflammatory biomarker testing was performed to test the effect of Organicell Flow on Covid 19 patients. ChartPad Software (Technomad), a cloud-based electronic data capture platform, was used to collect patient data. SOFA score was calculated as reported in the literature (Lambden S. et al., "The SOFA score-development, utility and challenges of accurate assessment in clinical trials," Crit Care. 23:374 (2019)) and was assessed on 0, 4, 6, 8, 14, 21, and 28 days after the initiation of Organicell Flow therapy. The SOFA score was derived from clinical and laboratory results obtained for respiration (PaO2/FiO2, mmHg), coagulation (platelets, ×10³/μL), liver (bilirubin, mg/dL), cardiovascular (mean arterial pressure), neurologic (Glasgow coma score), and renal (creatinine, mg/dL).

A portable chest x-ray (CXR) was used to acquire imaging at baseline and throughout treatment to evaluate, identify, and monitor lung abnormalities. After images were acquired, analysis was performed by the radiologist at Landmark Hospital and CXR reports were generated to outline the clinical findings.

Biomarker collection occurred at 0, 4, 6, 8, 14, 21, and 28 days after initiation of Organicell Flow therapy to assess for concentration of D-Dimer, CRP, IL2, IL6, and TNFa. D-Dimer and CRP measurements were performed at the Athens Regional Labs, while IL2, IL6, and TNFa were measured by Quest Diagnostics.

Glasgow Coma Scale (GCS) scores before and after treatment of Organicell Flow for all the patients were collected. GCS is a 15-point neurological scale used in assessing a patient's level of consciousness and level of neurologic functioning. It is a widely used scoring system for quantifying level of consciousness following traumatic brain injury. The total score is the sum of the scores in three categories, each of which is scored: best motor response, best verbal response, and eye opening.

Results

The clinical status of the patients was monitored for 28 days post-initiation of Organicell Flow therapy. After treatment, the respiratory status of the patients improved and stabilized. CU #1 respiratory status improved throughout the 28 days, changing from a 21% oxygen T-collar to roomair with no oxygen therapy requirement, CU #2 respiratory status improved during the 28 days with a transition from mechanical ventilation to non-mechanical ventilation, and the respiratory status of CU #3 improved 4 days post-treatment with decannulation and subsequent removal from oxygen therapy by day 14. Furthermore, all patients were transferred out of ICU status to the step-down unit within the 28-day period (Table 4). Patient CU #1 was discharged from the hospital 29 days post-treatment initiation and patient CU #3 was discharged from the hospital 26 days post-treatment initiation. Patient CU #2 remained in the hospital as she had experienced setbacks due to aspiration but was controlled and stable in the step-down unit with ventilation and hemodialysis.

TABLE 4

Clinical Status of Compassionate Use Patients

| Patient ID | CU#1 | CU#2 | CU#3 |
|---|---|---|---|
| Age | 74 | 79 | 66 |
| Gender | F | F | M |
| Weight (kg) | 118.75 | 100.24 | 60.36 |
| BMI (kg/m$^2$) | 38.43 | 40.18 | 22.14 |
| Prior comorbidities | Obesity, HTN, T2DM, depression, HLD, Vit. D deficiency | Obesity, HTN, HLD, Hodgkin's disease, HYT, status post left carotid endarterectomy | T2DM, HTN |
| Pre-treatment complications | Hyperglycemia Acute lung injury (ARDS) Anemia with normocytic indices | Hyperglycemia Acute renal failure Anemia requiring blood transfusion Acute lung injury (ARDS) | Acute renal injury Acute renal failure Acute lung injury (ARDS) Hyperglycemia |
| Days hospitalized Prior to treatment | 44 | 48 | 42 |
| Respiratory status | Base: 21% T-Collar<br>Day 4: 21% T-Collar<br>Day 6: 21% T-Collar<br>Day 8: 21% T-Collar<br>Day 14: 21% T-Collar<br>Day 21: PMV room air<br>Day 28: room air | Base: CPAP 5 PS 10 30%<br>Day 4: CPAP 5 PS 10 35%. Weaned PS to 8 and FiO$_2$ to 30%<br>Day 6: CPAP PS 40%<br>Day 8: Patient placed on 40% ATC at 0811 and the PMV at 1531<br>Day 14: Patient placed on 40% ATC at 0811 and the PMV at 1531<br>Day 21: 40% T-Collar<br>Day 28: 30% T-Collar | Base: PS/CPAP 8/5 24%<br>Day 4: Patient tolerates trial cap and is successfully decannulated<br>Day 8: Placed on 2 L of O2<br>Day14: Weaned down to room air<br>Day 21: Remains in room air<br>Day 28: Discharged 26 days after baseline |
| Status after 28-day follow up period | Decannulated, discharged | Step-down unit, remained in ventilation and hemodialysis | Decannulated, not in hemodialysis, discharged |

HTN, hypertension;
T2DM, type-2 diabetes;
HLD, hyperlipidemia;
HYT, hypothyroidism Effect on SOFA Score Improvement in SOFA score was found in all patients. SOFA score calculations decreased from 3 to 0 in CU #1 within 28 days, from 7 to 4 in CU #2 within 28 days, and from 4 to 0 in CU #3 within 21 days (Table 5). Assessment of the individual parameters used to calculate SOFA score showed improvements in PaO2/FiO2 and Glasgow score for CU #1, improvements in Glasgow score and creatinine levels for CU #2, and improvements in PaO2/FiO2 and creatinine levels for CU #3 (Table 5). Platelet count, bilirubin, and MAP measurements remained stable throughout the treatment course.

TABLE 5

SOFA score parameters

| Patient | SOFA Score | PaO$_2$/FiO$_2$ | Platelet Count (×10$^3$) | Bilirubin (mg/dL) | Glasgow score | MAP (mmHg) | Creatinine (mg/dL) |
|---|---|---|---|---|---|---|---|
| CU #1 | Day 0: 3 | Day 0: 342 | Day 0: 310 | Day 0: 0.5 | Day 0: 10-12 | Day 0: 77-103 | Day 0: 0.78 |
|  | Day 4: 2 | Day 4: 457 | Day 4: 364 | Day 4: 0.7 | Day 4: 10-12 | Day 4: 65-86 | Day 4: 1.10 |
|  | Day 6: 1 | Day 6: 466 | Day 6: 340 | Day 6: 0.6 | Day 6: 13-14 | Day 6: 92-96 | Day 6: 0.89 |
|  | Day 8: 1 | Day 8: 476 | Day 8: 329 | Day 8: 0.6 | Day 8: 13-14 | Day 8: 74-94 | Day 8: 0.98 |
|  | Day 14: 0 | Day 14: 462 | Day 14: 405 | Day 14: 0.6 | Day 14: 15 | Day 14: 79 | Day 14: 0.89 |
|  | Day 21: 0 | Day 21: 471 | Day 21: 423 | Day 21: 0.7 | Day 21: 15 | Day 21: 75 | Day 21: 0.94 |
|  | Day 28: 0 | Day 28: 471 | Day 28: 342 | Day 28: 0.6 | Day 28: 15 | Day 28: 95 | Day 28: 0.97 |
| CU #2 | Day 0: 7 | Day 0: 242 | Day 0: 183 | Day 0: 0.4 | Day 0: 10-12 | Day 0: 62-94 | Day 0: 3.55 |
|  | Day 4: 7 | Day 4: 268 | Day 4: 204 | Day 4: 0.3 | Day 4: 10-12 | Day 4: 76-92 | Day 4: 3.74 |
|  | Day 6: 4 | Day 6: 280 | Day 6: 190 | Day 6: 0.5 | Day 6: 15 | Day 6: 85-95 | Day 6: 1.98 |
|  | Day 8: 3 | Day 8: 232 | Day 8: 201 | Day 8: 0.4 | Day 8: 15 | Day 8: 73-96 | Day 8: 1.79 |

TABLE 5-continued

SOFA score parameters

| Patient | SOFA Score | PaO$_2$/FiO$_2$ | Platelet Count (×10$^3$) | Bilirubin (mg/dL) | Glasgow score | MAP (mmHg) | Creatinine (mg/dL) |
|---|---|---|---|---|---|---|---|
| | Day 14: 4 | Day 14: 245 | Day 14: 214 | Day 14: 0.3 | Day 14: 15 | Day 14: 93 | Day 14: 3.28 |
| | Day 21: 4 | Day 21: 240 | Day 21: 201 | Day 21: 0.3 | Day 21: 15 | Day 21: 82 | Day 21: 2.29 |
| | Day 28: 4 | Day 28: 271 | Day 28: 269 | Day 28: 0.3 | Day 28: 15 | Day 28: >70 | Day 28: 2.27 |
| CU #3 | Day 0: 4 | Day 0: 350 | Day 0: 428 | Day 0: 0.3 | Day 0: 15 | Day 0: 90 | Day 0: 3.96 |
| | Day 4: 3 | Day 4: 466 | Day 4: 540 | Day 4: 0.3 | Day 4: 15 | Day 4: 89 | Day 4: 4.16 |
| | Day 6: — | Day 6: — | Day 6: — | Day 6: — | Day 6: — | Day 6: — | Day 6: — |
| | Day 8: 3 | Day 8: 471 | Day 8: 723 | Day 8: 0.6 | Day 8: 15 | Day 8: 99 | Day 8: 5.2 |
| | Day 14: 2 | Day 14: 471 | Day 14: 507 | Day 14: 0.3 | Day 14: 15 | Day 14: 85 | Day 14: 2.73 |
| | Day 21: 0 | Day 21: 467 | Day 21: 294 | Day 21: 0.3 | Day 21: 15 | Day 21: 84 | Day 21: 1.24 |
| | Day 28: — | Day 28: — | Day 28: — | Day 28: — | Day 28: — | Day 28: — | Day 28: — |

Effect on Lung Imaging

Figure 25:
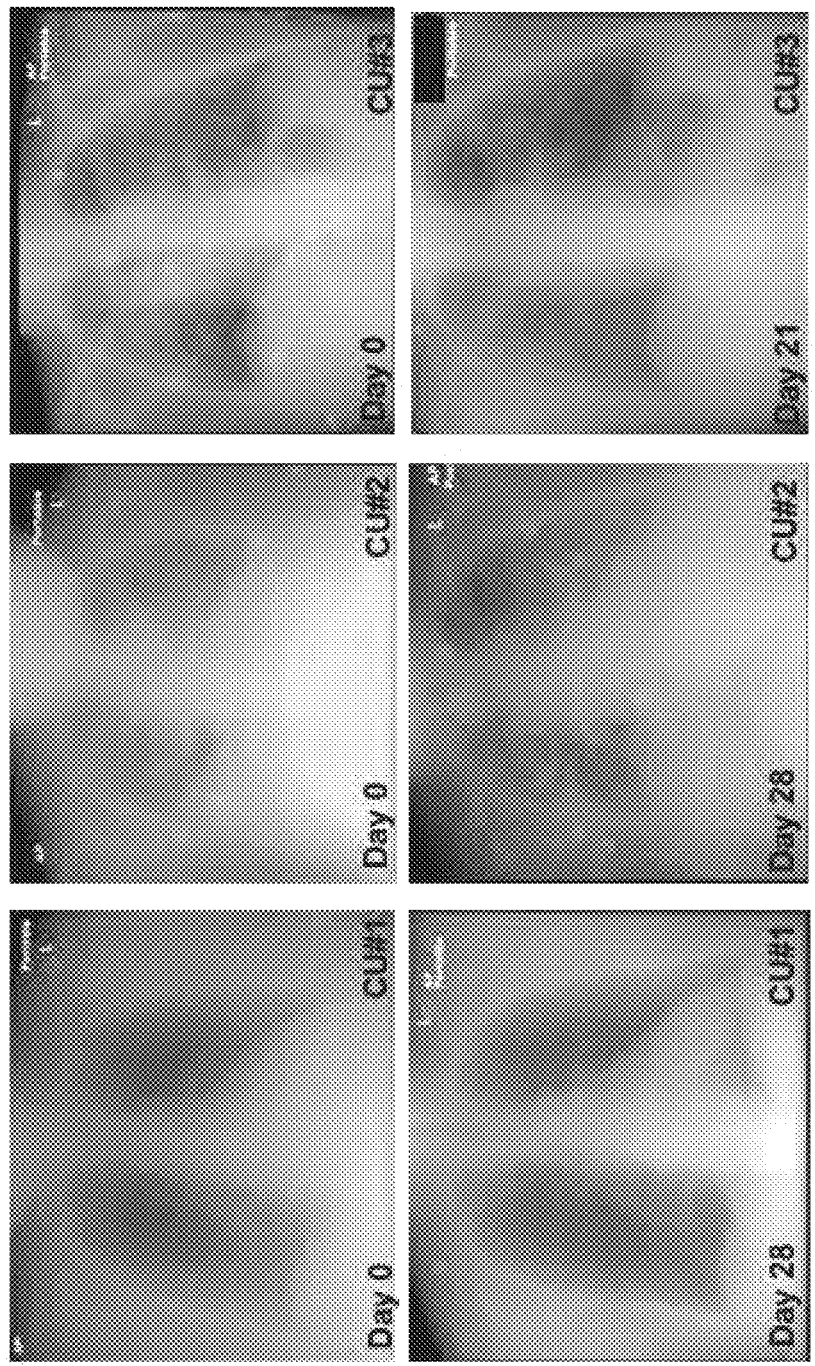
FIG. 25 shows Chest-X ray images. Chest-X ray images of patient CU #1 at day 0 and day 28 (Left). Chest-X ray images of patient CU #2 at day 0 and day 28 (Middle). Chest-X ray images of patient CU #3 at day 0 and day 21 (Right).

CXR images were collected throughout the treatment and the changes from baseline to day 21 and 28 were observed and reported (FIG. 25). CXR analysis of patient CU #1 displayed at baseline show an infiltrate present in the left lower lobe with no defined pleural fluid. After 28 days, CXR showed basilar, infrahilar air space opacity present bilaterally in the base of the lungs. CXR analysis of patient CU #2 displayed bilateral pulmonary disease at baseline. At day 28, CXR analysis showed small pleural effusions. CXR analysis of patient CU #3 displayed bilateral upper lobe infiltrate at baseline. At day 21, CXR analysis showed residual consolidation present in the left perihilar region. There was partial interval resolution of right upper lobe pneumonic consolidation.

Inflammatory Biomarker Assessment

Quantification of inflammatory biomarkers was completed at each testing time point (Table 6). There was a slight increase in TNFa for CU #1 within 28 days. CU #1 had an elevation in CRP and IL-6 that was attributed to bacteremia from an infected vein port at day 4, 6, and 8. However, levels of CRP and IL-6 began to drop below baseline by day 14 through day 28. Additionally, D-Dimer concentration decreased in this patient on day 28. CU #2 also showed a decrease in CRP and IL-6 levels by day 14 through day 28, however, TNFa and D-Dimer remained elevated. CU #3 showed high levels of inflammatory markers TNFa, IL-6, and D-Dimer up to day 8, however, declines in all markers were reported by day 21.

TABLE 6

Inflammatory biomarkers

| Patient | D-Dimer (ng/mL) | CRP (mg/dL) | IL6 (pg/mL) | IL2 (pg/mL) | TNFα (pg/mL) |
|---|---|---|---|---|---|
| CU #1 | Day 0: 1,033 | Day 0: 2.66 | Day 0: 19.39 | Day 0: <38.0 | Day 0: 0.95 |
| | Day 4: 1,113 | Day 4: >8.00 | Day 4: 50.83 | Day 4: <38.0 | Day 4: 2.06 |
| | Day 6: 1,069 | Day 6: >8.00 | Day 6: 51.95 | Day 6: <38.0 | Day 6: 2.08 |
| | Day 8: 1,165 | Day 8: >8.00 | Day 8: 40.29 | Day 8: <38.0 | Day 8: 2.29 |
| | Day 14:1,122 | Day 14: 1.28 | Day 14: 8.23 | Day 14: <38.0 | Day 14: 2.58 |
| | Day 21: 963 | Day 21: 0.93 | Day 21: 7.70 | Day 21: <38.0 | Day 21: 2.97 |
| | Day 28: 599 | Day 28: 0.70 | Day 28: 6.43 | Day 28: <38.0 | Day 28: 1.36 |
| CU #2 | Day 0: 5,871 | Day 0: 1.74 | Day 0: 23.62 | Day 0: <38.0 | Day 0: 1.77 |
| | Day 4: 4,305 | Day 4: 1.79 | Day 4: 22.17 | Day 4: <38.0 | Day 4: 1.99 |
| | Day 6: 2,377 | Day 6: 2.49 | Day 6: — | Day 6: — | Day 6: — |
| | Day 8: 1,980 | Day 8: 4.19 | Day 8: 32.82 | Day 8: <38.0 | Day 8: 1.69 |
| | Day 14: 3,444 | Day 14: 1.04 | Day 14: 17.79 | Day 14: <38.0 | Day 14: 2.13 |
| | Day 21: 3,627 | Day 21: 0.59 | Day 21: 16.57 | Day 21: <38.0 | Day 21: 1.90 |
| | Day 28: 4,468 | Day 28: 0.35 | Day 28: 13.58 | Day 28: <38.0 | Day 28: 2.21 |
| CU #3 | Day 0: 1,098 | Day 0: 6.48 | Day 0: 29.78 | Day 0: <38.0 | Day 0: 7.85 |
| | Day 4: 1,130 | Day 4: 2.15 | Day 4: 28.71 | Day 4: <38.0 | Day 4: 6.51 |
| | Day 6: — | Day 6: — | Day 6: — | Day 6: — | Day 6: — |
| | Day 8: 1,082 | Day 8: 1.98 | Day 8: 1,259 | Day 8: <38.0 | Day 8: >10 |
| | Day 14: 1,647 | Day 14: 2.79 | Day 14: 7.9 | Day 14: <38.0 | Day 14: 6.53 |
| | Day 21: 828 | Day 21: 0.18 | Day 21: 7.12 | Day 21: <38.0 | Day 21: 4.67 |
| | Day 28: — | Day 28: — | Day 28: — | Day 28: — | Day 28: — |

— sample not taken

Glasgow scores for all the patients before or after treatment were collected (Table 7).

TABLE 7

Glasgow Score

| Patient | Glasgow Score |
|---|---|
| CU#1 | Day 0: 10-12 |
| | Day 4: 10-12 |
| | Day 6: 13-14 |
| | Day 8: 13-14 |
| | Day 14: 15 |
| | Day 21: 15 |
| | Day 28: 15 |
| CU#2 | Day 0: 10-12 |
| | Day 4: 10-12 |
| | Day 6: 15 |
| | Day 8: 15 |
| | Day 14: 15 |
| | Day 21: 15 |
| | Day 28: 15 |

TABLE 7-continued

Glasgow Score

| Patient | Glasgow Score |
|---|---|
| CU#3 | Day 0: 15 |
| | Day 4: 15 |
| | Day 6: — |
| | Day 8: 15 |
| | Day 14: 15 |
| | Day 21: 15 |
| | Day 28: — |

Analysis of the collective data in all patients showed a reduction of SOFA score, improvement in ICU clinical status, improvement in Glasgow scores, and respiratory improvements. In addition, the patient's laboratory results have shown improvements with decreased inflammatory biomarkers.

The clinical features of patient CU #1 improved considerably with lungs improving on CXR and both mental status and kidney function returning to normal. Respiratory function of this patient improved 21 days post-treatment, transitioning from a 21% T-collar to room air PMV and decannulation on day 26, representing a considerable achievement for this patient demographic. Inflammatory marker status of this patient, IL6 and CRP, improved after the 14-day time point. The patient further improved to hospital discharge after 29 days posttreatment initiation. Glasgow scores of CU #1 improved to 15 after treatment.

The clinical features of patient CU #2 systemically improved, including respiratory function, during the treatment time course. The patient transitioned from CPAP 5 PS 10 30% ventilation to 30% T-Collar ventilation by day 28 and the acute delirium improved. This patient sustained acute kidney injury and required regular hemodialysis during the study period. Glasgow scores of CU #2 improved to 15 after treatment.

After receiving Organicell Flow, patient CU #3 displayed rapid improvement in respiratory function, with a complete decannulation from oxygen therapy by day 4. The patient had a complete recovery of renal function, had decreased creatinine concentration levels, and was removed from hemodialysis by day 17. CU #3 was discharged 26 days post-treatment initiation.

These completed case studies demonstrated human amniotic fluid-derived nanoparticles as a safe and efficacious therapeutic treatment to recover from complications induced by COVID-19 infection. The multidose administration of Organicell Flow as a therapeutic approach for patients severely ill from COVID-19 was safe and well tolerated, without the report of any serious adverse events. The molecular composition of Organicell Flow, particularly the nanoparticle population that includes perinatal secreted extracellular vesicles and exosomes, work as a therapeutic to COVID-19 patients. This study demonstrates the first use of an amniotic fluid-derived product in humans as a therapeutic to aid in the recovery from severe organ injuries induced by COVID-19 infection.

The entirety of each patent, patent application, publication or any other reference or document cited herein hereby is incorporated by reference. In case of conflict, the specification, including definitions, will control.

Citation of any patent, patent application, publication or any other document is not an admission that any of the foregoing is pertinent prior art, nor does it constitute any admission as to the contents or date of these publications or documents.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All of the features disclosed herein may be combined in any combination. Each feature disclosed in the specification may be replaced by an alternative feature serving a same, equivalent, or similar purpose. Thus, unless expressly stated otherwise, disclosed features (e.g., antibodies) are an example of a genus of equivalent or similar features.

As used herein, all numerical values or numerical ranges include integers within such ranges and fractions of the values or the integers within ranges unless the context clearly indicates otherwise. Further, when a listing of values is described herein (e.g., about 50%, 60%, 70%, 80%, 85% or 86%) the listing includes all intermediate and fractional values thereof (e.g., 54%, 85.4%). Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

Some embodiments of the technology described herein suitably can be practiced in the absence of an element not specifically disclosed herein. Accordingly, in some embodiments the term "comprising" or "comprises" can be replaced with "consisting essentially of" or "consisting of" or grammatical variations thereof. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. The term, "substantially" as used herein refers to a value modifier meaning "at least 95%", "at least 96%", "at least 97%", "at least 98%", or "at least 99%" and may include 100%. For example, a composition that is substantially free of X, may include less than 5%, less than 4%, less than 3%, less than 2%, or less than 1% of X, and/or X may be absent or undetectable in the composition.

I claim:

1. A therapeutic composition comprising:
   (a) a modified human amniotic fluid (HAF), the modified HAF comprising particles having a particulate size of less than about 200 nm,
   (b) HAF-derived nanoparticles selected from a list of nanoparticles consisting of exosomes, surface-bound proteins, and microRNAs (miRNAs);
   wherein said composition is substantially free of cells, lanugo, and *vernix,*
   wherein each of the HAF-derived nanoparticles has a diameter greater than about 30 nm, and
   wherein the concentration of particles in said composition is at least about $1 \times 10^8$ particles/ml.

2. The composition of claim 1, wherein the concentration of particles in said composition is at least about $1 \times 10^9$ particles/ml.

3. The composition of claim 2, wherein the concentration of particles in said composition is at least about $1 \times 10^{11}$ particles/ml.

4. The composition of claim 3, wherein the concentration of particles in said composition is in a range of about $2 \times 10^{11}$ particles/ml to about $1.1 \times 10^{12}$ particles/ml.

5. The composition of claim 1, wherein each of the HAF-derived nanoparticles have a diameter in a range of about 50 nm to about 250 nm.

6. The composition of claim 5, wherein each of the HAF-derived nanoparticles is less than about 1000 nm in size.

7. The composition of claim 1, wherein the HAF-derived nanoparticles comprise membrane encapsulated extracellular vesicles.

8. The composition of claim 1, wherein the HAF-derived nanoparticles comprise surface-bound protein CD63.

9. The composition of claim 8, wherein said composition comprises CD63 at a concentration of at least about 10 μg/ml.

10. The composition of claim 1, wherein the HAF-derived nanoparticles comprise three or more surface-bound proteins selected from a group consisting of CD9, CD63, CD81, CD326 and CD133.

11. The composition of claim 10, wherein the HAF-derived nanoparticles further comprise two or more surface-bound proteins selected from CD14, CD24, CD42a, CD44, CD29, CD14 and CD146.

12. The composition of claim 11, wherein the HAF-derived nanoparticles further comprise surface bound proteins HLA-DR, HLA-DP and HLA-DQ.

13. The composition of claim 1, wherein the HAF-derived nanoparticles comprise at least one miRNA selected from Table 1.

14. The composition of claim 13, wherein the HAF-derived nanoparticles comprise five or more miRNAs selected from hsa-let-7b, hsa-mir-200c, hsa-mir-30d, hsa-mir-125a, hsa-mir-483, hsa-mir-34c, hsa-mir-200a, hsa-mir-148a, hsa-mir-191, hsa-mir-21, hsa-mir-146a, hsa-mir-26b, hsa-mir-92b, hsa-mir-342, hsa-mir-34b, hsa-mir-423, hsa-mir-205, hsa-mir-203a, hsa-mir-99b, hsa-mir-375, hsa-mir-10b, hsa-mir-449c, hsa-mir-320a, and hsa-let-7f-2.

15. The composition of claim 13, wherein the HAF-derived nanoparticles comprise ten or more miRNAs selected from hsa-let-7b, hsa-mir-200c, hsa-mir-30d, hsa-mir-125a, hsa-mir-483, hsa-mir-34c, hsa-mir-200a, hsa-mir-148a, hsa-mir-191, hsa-mir-21, hsa-mir-146a, hsa-mir-26b, hsa-mir-92b, hsa-mir-342, hsa-mir-34b, hsa-mir-423, hsa-mir-205, hsa-mir-203a, hsa-mir-99b, hsa-mir-375, hsa-mir-10b, hsa-mir-449c, hsa-mir-320a, hsa-let-7f-2, hsa-mir-23a, hsa-mir-27b, hsa-mir-93, hsa-mir-221, hsa-mir-425, hsa-mir-151a, hsa-mir-190b, hsa-mir-223, hsa-mir-1180, hsa-mir-184, hsa-mir-361, hsa-mir-182, hsa-mir-92a-1, hsa-mir-29a, hsa-mir-183, hsa-mir-204, hsa-mir-574, hsa-mir-532, hsa-mir-28, hsa-mir-744, hsa-mir-2110, hsa-mir-140, hsa-mir-1307, hsa-mir-193b, hsa-mir-660, hsa-mir-224, hsa-mir-196b, hsa-mir-339, hsa-mir-186, hsa-mir-3065, hsa-mir-378a, hsa-mir-16-1, hsa-mir-338, hsa-mir-126, hsa-mir-95, hsa-mir-142, hsa-mir-328, hsa-mir-335, hsa-mir-125b-2, hsa-mir-149, and hsa-mir-150.

16. The composition of claim 1, wherein the HAF-derived nanoparticles comprise hsa-mir-30d, hsa-mir-191, hsa-mir-21, and hsa-mir-146a.

17. The composition of claim 1, wherein the HAF-derived nanoparticles comprise two or more miRNAs selected from hsa-mir-30d, hsa-mir-191, hsa-mir-21, and hsa-mir-146a.

18. The composition of claim 1, wherein the HAF-derived nanoparticles comprise DNA polymerase beta, DNA polymerase lambda, telomerase reverse transcriptase, and RAD50.

19. The composition of claim 1, wherein said composition comprises hyaluronic acid at a concentration of at least about 200 ng/ml.

20. The composition of claim 19, wherein said composition comprises hyaluronic acid at a concentration of about 200 ng/ml to about 2000 ng/ml.

21. The composition of claim 19, wherein said composition comprises hyaluronic acid at a concentration of about 600 ng/ml to about 2000 ng/ml.

22. The composition of claim 1, wherein said composition is substantially free of bacteria, fungus and yeast.

23. The composition of claim 1, wherein said composition comprises at least one cytokine or growth factor selected from a group consisting of angiogenin (ANG), BLC, EGF, FGF-6, GCP-2, IGFBP-1, IGF-BP2, IGF-BP4, IL-1RA, IL-6, LEPTIN, MCP-1, MIG, MIP-1DELTA, NAP-2, adiponectin (ACRP30), GRO-A, HCC-4, HGF, ICAM-1, IGFBP-6, IL-1R4, IL-6R, IL-8, OPG, STNFRII, STNFRI, TIMP-1, TIMP-2, and UPAR.

24. The composition of claim 23, wherein said composition comprises ANG, IL-1RA, MCP-1, IL-6, UPAR, FGF-6, EGF, HGF, LEPTIN, and ACRP30.

25. The composition of claim 1, wherein said composition comprises at least one of ACRP30, AGRP, ANGPT2, AREG, AXL, B-NGF, BFGF, BTC, CCL28, CTAK, DTK, EGFR, ENA-78, FAS, FGF-4, FGF-9, G-CSF, GITR, GITR LIGAND, GRO, GRO-ALPHA, HCC-4, HGF, I-TAC, ICAM-1, ICAM-3, IGF-1SR, IGFBP-3, IGFBP-6, IL-11, IL-12 P40, IL-12 P70, IL-17, IL-1R1, IL-2R ALPHA, IL-6R, IL-8, IL1R4, MIF, MIP-1 ALPHA, MIP-2 BETA, MIP-3 BETA, MSP ALPHA, NT-4, OPG, OSM, PLGF, SGP130, STNFRI, STNFRII, TECK, THPO, TIMP-1, TIMP-2, TRAIL R3, TRAIL R4, UPAR, VEGF, VEGF-D, XCL1, ANG, BDNF, BLC, BMP4, BMP6, CCL23, CNTP, EGF, Eoxtanin 1, Eoxtanin 2, Eoxtaxin 3, FGF-6, FGF-7, FLT3-LIGAND, FRACTALKINE, GCP-2, GDNF, GMCSF, 1-309, IGF-1, IGFBP1, IGFBP2, IGFBP4, IL-10, IL-13, IL-15, IL-16, IL-1B, IL-1RA, IL-2, IL-3, IL-4, IL-5, IL-6, IL-7, IL1-A, INF GAMMA, LEPTIN, LIGHT, M-CSF, MCP-1, MCP-2, MCP-3, MCP4, MDC, MIG, MIP-1A, MIP-3A, NAP-2, NT-3, PARC, PDGFBB, RANTES, SCF, SDF1A, TARC, TGF-B1, TGF-B3, TNFA, and TNFB.

26. The composition of claim 1, wherein the at least one nanoparticle comprises CD9+ and CD63+ at a concentration of at least about 10 µg/ml.

27. The composition of claim 1, wherein the at least one nanoparticle comprises CD9+ and CD63+ at a concentration of at least about 200 µg/ml.

28. The composition of claim 1, wherein the at least one nanoparticle comprises CD9+ and CD63+ at a concentration of at least about 1000 µg/ml.

29. The composition of claim 1, wherein said composition suppresses t-cell activation and proliferation, macrophage migration, and human inflammatory responses.

30. A pharmaceutical composition comprising:
(i) a modified human amniotic fluid (HAF), the modified HAF having a particulate size of less than about 200 nm and having an amount of HAF; and
(ii) HAF-derived nanoparticles, the HAF-derived nanoparticles comprising at least one nanoparticle selected from a list of nanoparticles comprising exosomes, surface-bound proteins, and microRNAs (miRNAs);
wherein said composition is substantially free of cells, lanugo, and *vernix*,
wherein each of the HAF-derived nanoparticles has a diameter greater than about 30 nm,
wherein the concentration of particles in said composition is at least about $1 \times 10^9$ particles/ml, and
(iii) one or more pharmaceutically acceptable ingredients, the one or more pharmaceutically acceptable ingredients comprising excipients and additives.

31. The pharmaceutical composition of claim 30, wherein said pharmaceutical composition is configured for administration via one or more methods of administration, the one or more methods of administration including oral administration, parenteral administration, administration via nebulization, and intravenous administration.

32. A method of treating a lung disease or lung disorder in a subject in need thereof, comprising administering an effective amount of the therapeutic composition of claim 1 to the subject, wherein the disease or disorder is selected from acute respiratory syndrome, chronic obstructive pulmonary disease (COPD) and bronchopulmonary dysplasia.

33. The method of claim 32, wherein the lung disease or lung disorder comprises chronic obstructive pulmonary disease (COPD).

34. The method of claim 32, wherein the lung disease or lung disorder comprises bronchopulmonary dysplasia (BPD).

35. The method of claim 32, wherein the lung disease or lung disorder comprises acute respiratory syndrome.

36. The method of claim 35, wherein the subject is infected with a coronavirus.

37. The method of claim 36, wherein the subject is infected with a COVID19 or SARS-associated coronavirus (SARS-COV2).

38. A method of treating acute brain injury in a subject in need thereof, comprising administering to the subject an effective amount of the composition of claim 1.

39. A method of treating acute organ failure in a subject in need thereof, comprising administering to the subject an effective amount of the composition of claim 1.

40. A method of treating arthritis in a subject in need thereof, comprising administering to the subject an effective amount of the composition of claim 1.

41. The method of claim 40, wherein the arthritis is osteoarthritis or rheumatoid arthritis.

42. The method of claim 40, wherein the composition is administered by intravenous or intraarticular injection.

43. The method of claim 40, wherein the subject is human.

* * * * *